US011653763B2

(12) United States Patent
Flanagan

(10) Patent No.: US 11,653,763 B2
(45) Date of Patent: *May 23, 2023

(54) ATHLETIC CHAIR WITH ADJUSTABLE HEATING AND HEIGHT

(71) Applicant: Deer Solutions LLC, Milwaukee, WI (US)

(72) Inventor: Troy Rohan Flanagan, Elm Grove, WI (US)

(73) Assignee: Deer Solutions LLC, Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/496,950

(22) Filed: Oct. 8, 2021

(65) Prior Publication Data

US 2022/0133041 A1 May 5, 2022

Related U.S. Application Data

(63) Continuation of application No. 16/790,511, filed on Feb. 13, 2020, now Pat. No. 11,140,987.

(Continued)

(51) Int. Cl.
*A47C 7/74* (2006.01)
*A47C 1/00* (2006.01)
(Continued)

(52) U.S. Cl.
CPC .................. *A47C 1/00* (2013.01); *A47C 3/20* (2013.01); *A47C 3/30* (2013.01); *A47C 7/748* (2013.01);
(Continued)

(58) Field of Classification Search
CPC .... A47C 1/00; A47C 3/20; A47C 3/30; A47C 7/748; A47C 11/005; A47C 1/124;
(Continued)

(56) References Cited

U.S. PATENT DOCUMENTS 1,526,132 A 2/1925 Gilger
3,323,833 A * 6/1967 Kasparian .............. A47C 7/004
248/188.7

(Continued)

FOREIGN PATENT DOCUMENTS

KR 101330611 B1 * 11/2019 ............. A47C 1/124

OTHER PUBLICATIONS

Cornell University Ergonomics Web, DEA 3250/6510 Class Notes, Ergonomics of Sitting, Sitting and Chair Design, printed from ergo.human.cornell.edu/DEA3250Flipbook/DEA3250notes/sitting.html on Mar. 10, 2020, 3 pages.

(Continued)

*Primary Examiner* — Rodney B White
(74) *Attorney, Agent, or Firm* — Foley & Lardner LLP

(57) ABSTRACT

A seating assembly for athletes includes seats having a back and seat portion, a base, an adjustable element, a user interface device, and a controller. The back portion includes a back heating member that provides heat to a user's torso. The seat portion includes a lower limb heating member that provides heat to the user's lower limbs. The base supports each seat. The adjustable element is coupled to the base and one of the seats and adjusts height of the seat. The user interface device receives an input regarding a desired temperature of the back heating member and the lower limb heating member. The controller receives the input and adjusts an operation of the back heating member and the lower limb heating member to achieve the desired temperature. The user interface device receives a second input to adjust the a height of the seat relative to the floor surface.

18 Claims, 22 Drawing Sheets

Related U.S. Application Data

(60) Provisional application No. 62/805,815, filed on Feb. 14, 2019.

(51) Int. Cl.
*A47C 3/20* (2006.01)
*A47C 11/00* (2006.01)
*A61G 15/00* (2006.01)
*A61F 7/00* (2006.01)
*A47C 3/30* (2006.01)

(52) U.S. Cl.
CPC .............. *A47C 11/005* (2013.01); *A61F 7/00* (2013.01); *A61F 7/007* (2013.01); *A61G 15/007* (2013.01); *A61F 2007/0024* (2013.01); *A61F 2007/0071* (2013.01); *A61F 2007/0093* (2013.01)

(58) Field of Classification Search
CPC .... A61F 7/00; A61F 7/007; A61F 2007/0024; A61F 2007/0071; A61F 2007/0093
USPC .......... 297/330, 180.1, 180.12, 217.3, 217.4, 297/217.5, 248
See application file for complete search history.

(56) References Cited

U.S. PATENT DOCUMENTS

| | | | |
|---|---|---|---|
| 3,866,973 A | 2/1975 | Heubeck | |
| 3,874,728 A | 4/1975 | Weiland | |
| 3,960,145 A | 6/1976 | Scarbrough | |
| 4,258,706 A | 3/1981 | Shank | |
| 4,306,747 A | 12/1981 | Moss | |
| 4,628,188 A | 12/1986 | Andreasson | |
| 4,969,684 A | 11/1990 | Zarotti | |
| 5,015,035 A | 5/1991 | Stoeckl | |
| 5,203,609 A | 4/1993 | Stoeckl | |
| 5,387,181 A | 2/1995 | Olsen | |
| 5,462,515 A | 10/1995 | Tseng | |
| 5,800,490 A | 9/1998 | Patz | |
| 5,807,177 A * | 9/1998 | Takemoto | A63F 13/08 463/47 |
| 5,839,788 A | 11/1998 | Orr, III | |
| 5,992,804 A * | 11/1999 | Johnson | B63B 29/06 114/364 |
| 5,992,934 A | 11/1999 | Gehrig et al. | |
| 6,095,992 A | 8/2000 | Augustine | |
| 6,243,635 B1 | 6/2001 | Swan | |
| 6,569,189 B1 | 5/2003 | Augustine et al. | |
| 6,702,767 B1 | 3/2004 | Douglas et al. | |
| 6,770,043 B1 | 8/2004 | Kahn | |
| 7,178,871 B1 | 2/2007 | Round et al. | |
| 7,744,153 B2 | 6/2010 | Gentry et al. | |
| 7,931,334 B1 | 4/2011 | Caruso | |
| 8,016,351 B2 | 9/2011 | Cassaday | |
| 8,348,872 B2 | 1/2013 | Lunter et al. | |
| 8,596,716 B1 | 12/2013 | Caruso | |
| 9,016,279 B2 * | 4/2015 | Guering | A62B 18/02 297/217.3 |
| 9,943,174 B1 * | 4/2018 | Jacobs | A61H 9/0078 |
| 10,433,646 B1 | 10/2019 | Schmidt | |
| 11,140,987 B2 * | 10/2021 | Flanagan | A47C 11/005 |
| 2002/0138901 A1 | 10/2002 | Augustine et al. | |
| 2002/0183667 A1 | 12/2002 | Kitadou et al. | |
| 2003/0088299 A1 | 5/2003 | Magers et al. | |
| 2003/0130601 A1 | 7/2003 | Kim | |
| 2004/0195874 A1 * | 10/2004 | Lee | A47C 31/126 297/217.3 |
| 2004/0225341 A1 | 11/2004 | Schock et al. | |
| 2005/0027218 A1 | 2/2005 | Filtvedt et al. | |
| 2005/0096714 A1 | 5/2005 | Freedman et al. | |
| 2007/0255362 A1 | 11/2007 | Levinson et al. | |
| 2008/0132976 A1 | 6/2008 | Kane et al. | |
| 2008/0182071 A1 | 7/2008 | Cheng | |
| 2010/0022926 A1 | 1/2010 | Kramer et al. | |
| 2010/0318004 A1 | 12/2010 | Numata et al. | |
| 2011/0251535 A1 | 10/2011 | Bender | |
| 2012/0095537 A1 | 4/2012 | Hall et al. | |
| 2012/0109232 A1 | 5/2012 | Mohn | |
| 2012/0215363 A1 * | 8/2012 | Menard | A63J 25/00 297/217.3 |
| 2013/0345778 A1 | 12/2013 | Woods | |
| 2014/0210236 A1 | 7/2014 | Ruf | |
| 2014/0222121 A1 | 8/2014 | Spence et al. | |
| 2014/0243938 A1 | 8/2014 | Mcpherson | |
| 2014/0358203 A1 | 12/2014 | Li | |
| 2014/0378880 A1 | 12/2014 | Arsenault et al. | |
| 2015/0237927 A1 | 8/2015 | Nelson et al. | |
| 2015/0289817 A1 | 10/2015 | Augustine et al. | |
| 2016/0038335 A1 | 2/2016 | Park et al. | |
| 2016/0143803 A1 | 5/2016 | Portales | |
| 2016/0183687 A1 | 6/2016 | Hoyt et al. | |
| 2017/0028196 A1 | 2/2017 | Stopperan | |
| 2017/0128258 A1 | 5/2017 | Diller et al. | |
| 2018/0193185 A1 | 7/2018 | Thomas et al. | |
| 2018/0271286 A1 * | 9/2018 | Jacobs | A47C 1/124 |
| 2018/0271287 A1 * | 9/2018 | Jacobs | A47C 1/124 |
| 2018/0289166 A1 | 10/2018 | Andon et al. | |
| 2018/0316213 A1 * | 11/2018 | Havell | A47C 1/022 |
| 2018/0361167 A1 | 12/2018 | De La Torre Barreiro | |
| 2019/0046350 A1 | 2/2019 | Anderson et al. | |
| 2019/0175393 A1 | 6/2019 | Lee et al. | |
| 2019/0269549 A1 | 9/2019 | Paek et al. | |
| 2019/0274914 A1 | 9/2019 | Hunter et al. | |
| 2019/0387884 A1 * | 12/2019 | Jacobs | A47C 7/622 |
| 2020/0085116 A1 | 3/2020 | Harris | |
| 2020/0093635 A1 | 3/2020 | Kakizaki et al. | |
| 2020/0214448 A1 * | 7/2020 | Jacobs | A47C 7/723 |
| 2020/0246180 A1 | 8/2020 | Liang et al. | |
| 2020/0260883 A1 * | 8/2020 | Jacobs | A47C 7/70 |
| 2020/0297965 A1 * | 9/2020 | Yoda | A61F 7/0053 |
| 2020/0352036 A1 * | 11/2020 | Jacobs | A47C 7/622 |
| 2021/0031821 A1 | 2/2021 | Dusa, II | |
| 2021/0052418 A1 | 2/2021 | Breiter | |
| 2021/0169234 A1 * | 6/2021 | Jacobs | H01R 24/78 |

OTHER PUBLICATIONS

Hamaoui et al., Sitting on a Sloping Seat Does Not Reduce the Strain Sustained by the Postural Chain, PLOS ONE, published Jan. 14, 2015, 14 pages.

Herman Miller, Inc., If the Chair Fits Research Summary, 2008, 5 pages.

Oyama et al., Measurement of Venous Blood Flow in the Lower Limbs: Prevention of Deep Vein Thrombosis during Prolonged Sitting, Work with Computing Systems, Kuala Lumpur: Damai Sciences, 2004, 6 pages.

* cited by examiner

ATHLETIC CHAIR WITH ADJUSTABLE HEATING AND HEIGHT

CROSS-REFERENCE TO RELATED PATENT APPLICATION

This application is a continuation of U.S. patent application Ser. No. 16/790,511, filed Feb. 13, 2020, now U.S. Pat. No. 11,140,987 B2, which claims the benefit of and priority to U.S. Provisional Patent Application No. 62/805,815, filed Feb. 14, 2019, all of which are hereby incorporated by reference herein in their entireties.

BACKGROUND

During sporting events, athletes often rest on chairs, benches, or seats. Many of these seating arrangements which the athletes rest on cause the players lower limbs to be put into a position which restricts venous blood flow, thereby hindering athletic performance. This may be particularly relevant for basketball players who are on average much taller than the average person.

SUMMARY

One implementation of the present disclosure is a seating assembly for one or more athletes, according to some embodiments. The seating assembly includes one or more seats. Each seat includes a back portion, a seat portion, a base, an adjustable element, a user interface device, and a controller. The back portion includes a back heating member configured to provide heat to a torso of a user. The seat portion includes a lower limb heating member configured to provide heat to lower limbs of the user. The base is configured to support each of the one or more seats. The adjustable element is coupled to the base at one end and coupled to one of the seats at an opposite end and configured to adjust a height of the seat relative to a floor surface. The user interface device is configured to receive an input regarding a desired temperature of at least one of the back heating member and the lower limb heating member. The controller is configured to receive the input and adjust an operation of at least one of the back heating member and the lower limb heating member to achieve the desired temperature. The user interface device is further configured to receive a second input to adjust the height of the seat relative to the floor surface.

In some embodiments, the back portion and the seat portion of each of the one or more seats form an angle greater than ninety degrees to facilitate venous blood flow to lower limbs of the user.

In some embodiments, the angle formed by the back portion and the seat portion is between 110 and 120 degrees.

In some embodiments, the heat provided to the torso and the heat provided to lower limbs are each provided at a temperature value between 38 and 45 degrees Celsius to facilitate venous blood flow of at least one of the torso and the lower limbs of the user and to facilitate maintaining a specific muscle temperature of the user.

In some embodiments, the back heating member and the lower limb heating member are configured to operate according to a maximum heating mode of operation, a medium heating mode of operation, and a low heating mode of operation.

In some embodiments, the back heating member is positioned within a cushion of the back portion and the seat heating member is positioned within a cushion of the seat portion.

In some embodiments, each seat is configured to increase in height relative to a floor surface at least ten inches to facilitate a popliteal height of at least 18 inches of a user.

In some embodiments, the adjustable element includes a prime mover configured to adjust the height of the seat relative to the floor surface. In some embodiments, the prime mover is any of an electric motor or a hydraulic system.

Another implementation of the present disclosure is a seating assembly for one or more athletes, according to some embodiments. The seating assembly includes multiple seats and a base. Each seat includes a back portion, a seat portion, and a controller. The back portion includes a back cushion and a back heating element positioned within the back cushion. The back heating element and the back cushion are configured to transfer heat to a torso of a user. The seat portion includes a seat cushion and a seat heating element positioned within the seat cushion. The seat heating element and the seat cushion are configured to transfer heat to lower limbs of the user. The controller is configured to receive an input regarding a desired temperature of at least one of the back heating element and the seat heating element and further configured to operate the back heating element and the seat heating elements. A height of each seat is adjustable to maintain a popliteal height of at least 18 inches of the user. The base is fixedly coupled with an adjustable support member of each of the multiple seats.

In some embodiments, the back heating element and the seat heating element are configured to operate according to a maximum heating mode of operation, a medium heating mode of operation, and a low heating mode of operation.

In some embodiments, each seat is configured to adjust in height at least 10 inches between a minimum height and a maximum height.

In some embodiments, the base further includes multiple openings configured to receive one or more elongated members of a transportation mechanism for movement of the seating assembly.

In some embodiments, the back portion and the seat portion of each seat form an angle greater than ninety degrees to facilitate venous blood flow to the lower limbs of the user.

In some embodiments, the angle is between 110 and 120 degrees.

In some embodiments, the back heating element is configured to heat the torso of the user to a temperature between 38 and 45 degrees Celsius to facilitate venous blood flow to the torso of the user and the seat heating element is configured to heat the lower limbs of the user to a temperature between 38 and 45 degrees Celsius to facilitate venous blood flow to the lower limbs of the user.

Another implementation of the present disclosure is a method for installing and operating a seating assembly with adjustable heating and adjustable height, according to some embodiments. The method includes providing a seating assembly having multiple seats. Each seat is configured to provide adjustable heating and adjustable height for a user. The method includes positioning the seating assembly in a desired location. The method also includes connecting the seating assembly to a power source for the adjustable heating and the adjustable height of each of the multiple seats. The method also includes receiving a command of an adjustment of height and heat from a user interface of at least one of the multiple seats. The method also includes adjusting an amount of heat provided to the user via one or more heating pads disposed within a back portion and a seat portion of the seat of one of the multiple seats based on the received heat command. The method also includes adjusting a height of at least one of the seats based on the received height command. In some embodiments, adjusting the height of the seat includes increasing a distance between the seat portion and a floor surface between a minimum value of the distance and a maximum value of the distance.

In some embodiments, the back portion and the seat portion of each of the multiple seats form an angle greater than ninety degrees.

In some embodiments, the angle formed by the back portion and the seat portion is between 110 and 120 degrees to improve venous blood flow to lower limbs of the user.

In some embodiments, the heat provided to the user is provided to heat at least one of the torso and the lower limbs of the user to a temperature between 38 and 45 degrees Celsius to facilitate venous blood flow.

In some embodiments, the method further includes inserting one or more fork members into one or more apertures of a base of the seating assembly, and lifting the seating assembly via the one or more fork members inserted into the one or more apertures of the base of the seating assembly for removal and placement of the seating assembly.

DETAILED DESCRIPTION

Before turning to the figures, which illustrate the exemplary embodiments in detail, it should be understood that the present disclosure is not limited to the details or methodology set forth in the description or illustrated in the figures. It should also be understood that the terminology used herein is for the purpose of description only and should not be regarded as limiting.

Overview

Referring generally to the FIGURES, an adjustable heating and adjustable height seating assembly for athletes is shown, according to an exemplary embodiment. The heatable seating assembly may include heating pads configured to deliver heat to the athlete's torso and lower limbs. The heating pads may be independently controlled so that different amounts of heat are provided to the athlete's torso and lower limbs or may be operated to provide a same amount of heating to the user's torso and lower limbs. The heat provided to the athlete's torso and lower limbs may be individually manually adjusted by the athletes (e.g., via a user input, pressing a button, turning a dial, etc.). Additionally, each seat of the seating assembly may include individual controls for adjusting either one of or both the heat provided to the torso and lower limbs. Each seat of the seating assembly also includes height adjustment. The athletes may individually adjust the height of each seat, thereby achieving a height (e.g., popliteal height) that does not restrict venous blood flow. Additionally, the heat provided to the torso and lower limbs of the athletes can improve venous blood flow. Improving venous blood flow of the athletes can advantageously improve athletic performance.

Seating Assembly

Figure 1:
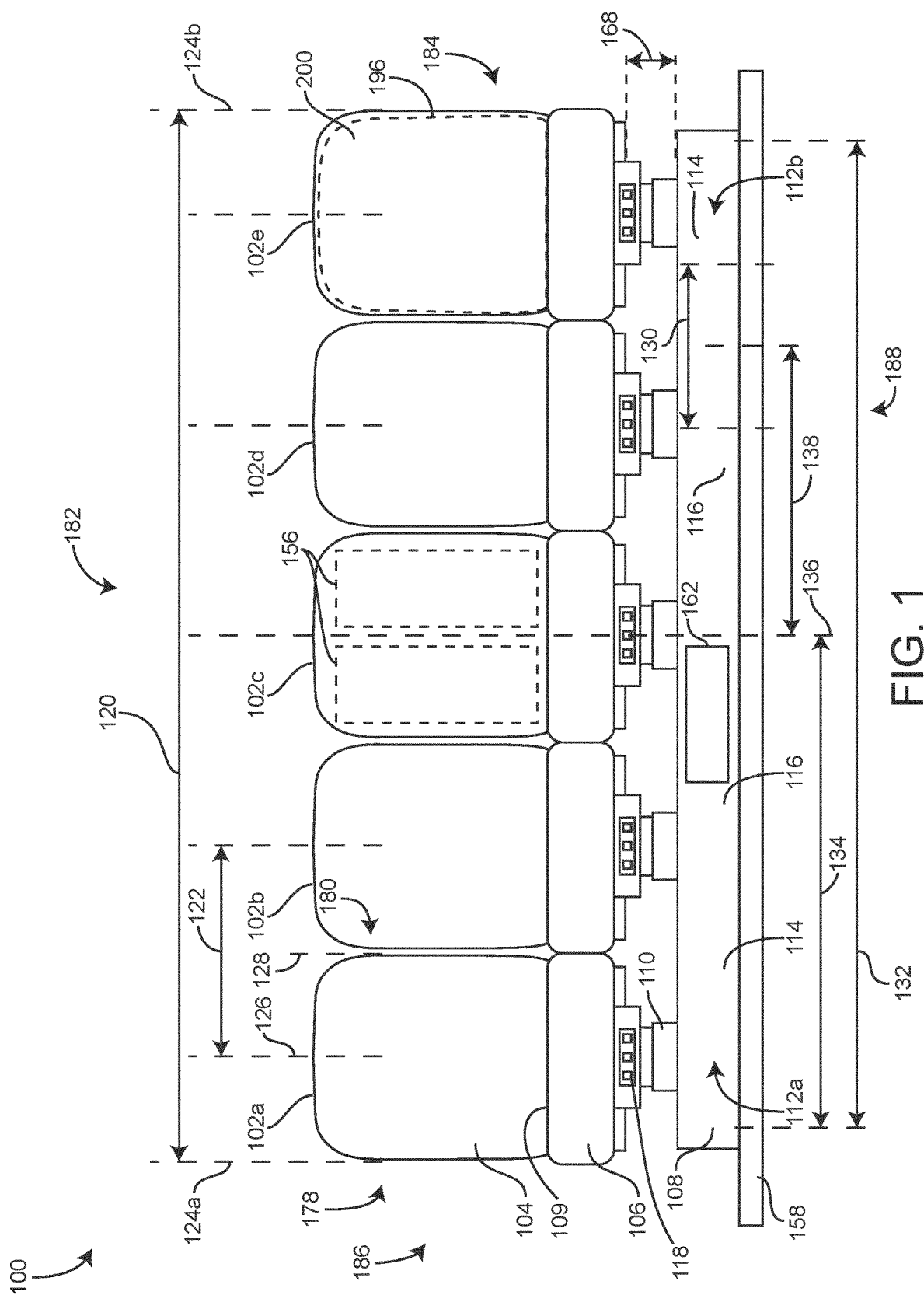
FIG. 1 is a front view of a seating assembly, according to an exemplary embodiment.
Figure 2:
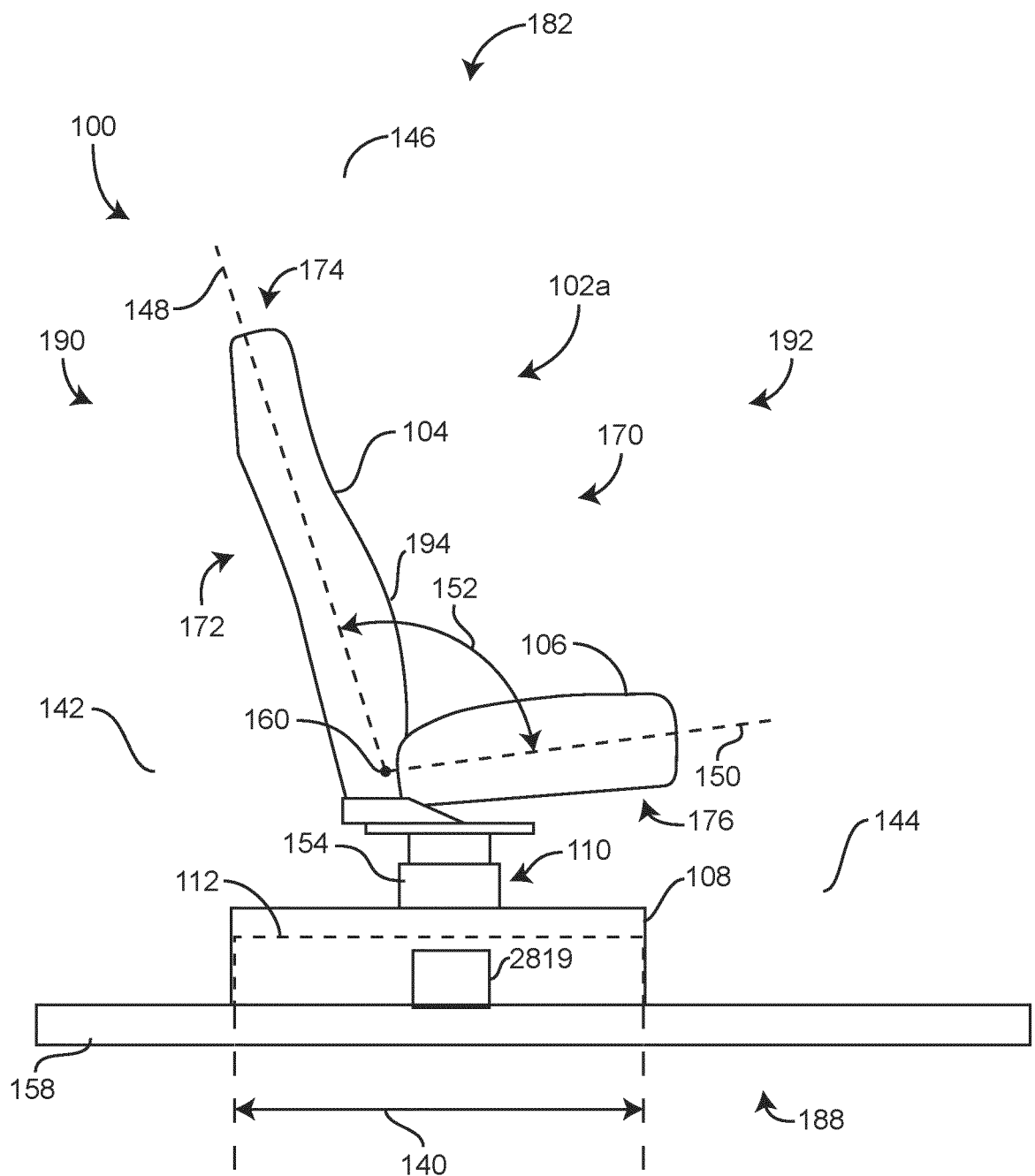
FIG. 2 is side view of the seating assembly of FIG. 1, according to an exemplary embodiment.
Figure 3:
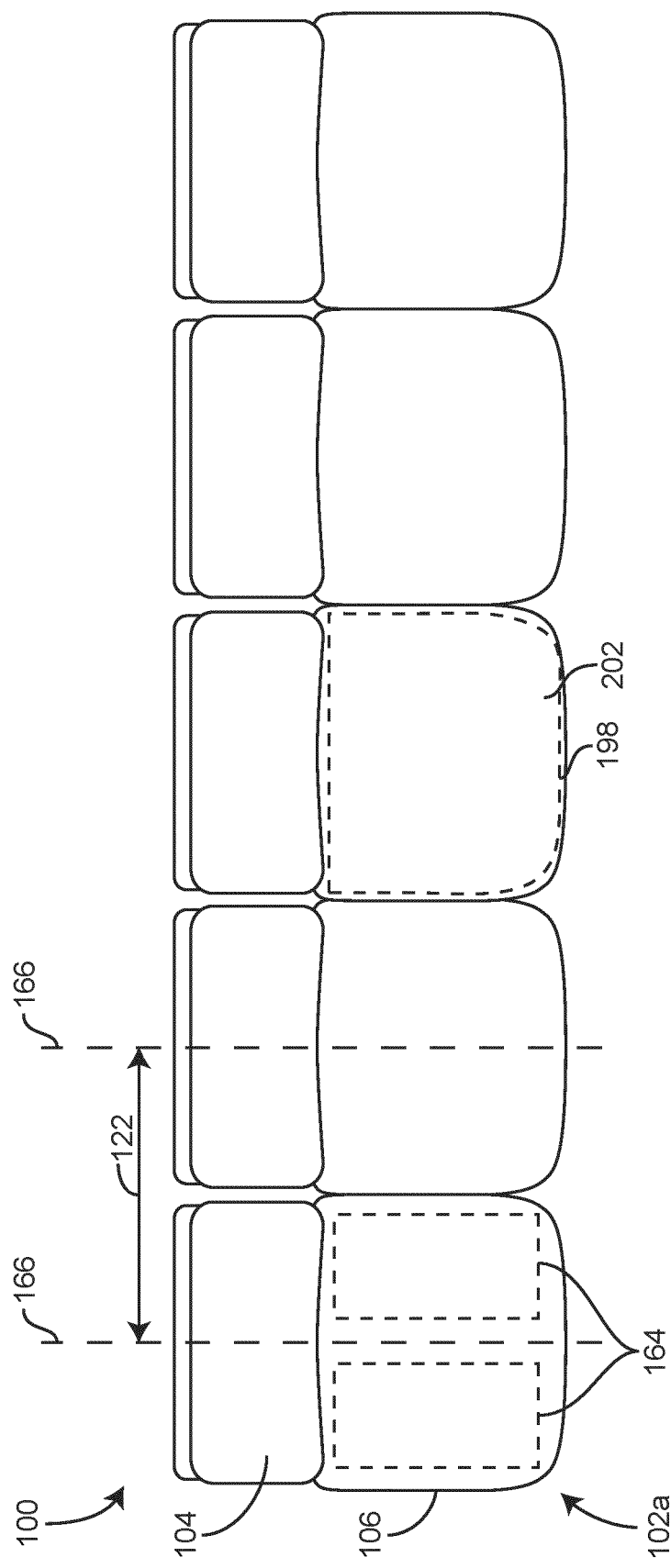
FIG. 3 is a top view of the seating assembly of FIG. 1, according to an exemplary embodiment.

Referring now to FIGS. 1-5, a chair assembly (e.g., a seating arrangement, a seating assembly, a bench, etc.), shown as seating assembly 100 is shown, according to an exemplary embodiment. Seating assembly 100 is configured to provide one or more individuals (e.g., persons, athletes, basketball players, etc.), with one or more surfaces to sit upon. Seating assembly 100 includes a base (e.g., a base, a frame, a structure, a block, etc.) shown as base 108, one or more seats (e.g., chairs), shown as seats 102, and one or more adjustable pillars (e.g., telescoping pillars, pedestals, shafts, upright members, bars, etc.), shown as adjustable support members 110. Base 108 rests upon a floor surface (e.g., a basketball court, a ground surface, a floor, etc.), shown as floor 158. In some embodiments, base 108 rests upon floor 158 and is removably (e.g., via fasteners) coupled to floor 158. In some embodiments, base 108 is fixed relative to floor 158. In other embodiments, base 108 rests upon floor 158 and frictional forces between a bottom surface of base 108 and floor 158 prevent seating assembly 100 from moving (e.g., translating, rotating) along floor 158. Seating assembly 100 includes a front side 192, a rear or back side 190, a left side 184, a right side 186, a top side 182, and a bottom side 188. In an exemplary embodiment, seating assembly 100 includes five seats 102. Seating assembly 100 may include more or less than five seats 102, according to other embodiments. As shown in FIG. 3, seats 102 may be aligned on base 108 (e.g., in a line). Seats 102 may also be positioned on base 108 directly adjacent each other so that adjacent or neighboring seats 102 abut, contact, etc., each other.

Seating assembly 100 has an overall length 120, according to an exemplary embodiment. Length 120 may be measured between outermost surfaces of seat 102*a* and seat 102*e*, according to an exemplary embodiment. Length 120 may be 2500 mm, according to some embodiments. Each of seats 102*a*-102*e* are disposed distance 122 apart. Distance 122 may be defined as a distance between central axis 126 of a first seat (e.g., seat 102*a*) and a central axis 126 of an adjacent seat (e.g., seat 102*b*). Distance 122 may be 500 mm, according to some embodiments. Seats 102*a*-102*e* are positioned adjacent each other such that there are no gaps between adjacent seat portions 106, according to some embodiments. Advantageously, this reduces the likelihood of finger entrapment between adjacent seats 102. Since seats 102 are adjacent each other, an overall width of each seat 102 is substantially equal to distance 122 (e.g., 500 mm). In some embodiments, length 120 is defined between axis 124*a* and axis 124*b*, where axis 124*a* is a vertical axis which intersects a right most surface of seating assembly 100 and axis 124*b* is a vertical axis which intersects a left most surface of seating assembly 100.

Base 108 is coupled to each of adjustable support members 110 of seats 102. Adjustable support members 110 may be rotationally fixed relative to base 108, such that seats 102 cannot rotate relative to base 108. Adjustable support members 110 protrude outwards from base 108 towards top side 182 of seating assembly 100. Adjustable support members 110 may protrude a distance into an aperture of base 108 (i.e., towards bottom side 188) to provide support for seats 102. In some embodiments, adjustable support members 110 are coupled (e.g., fixedly, removably, connected via fasteners, etc.) to base 108. Seats 102 are coupled (e.g., removably coupled, fixedly connected, mounted, etc.) to adjustable support members 110. Therefore, as adjustable support members 110 increase or decrease in height, seats 102 are raised or lowered relative to floor 158.

Adjustable support members 110 are configured to adjust a height of seats 102. For example, as shown in FIG. 1, there is a distance 168 between an upper surface of base 108 and a bottom surface of seat 102*e*. The adjustable support member 110 of seat 102*e* is configured to increase or decrease distance 168. In some embodiments adjustable support members 110 are telescoping pedestals, configured to increase in length and decrease in length, thereby increasing or decreasing distance 168. In an exemplary embodiment, each of seats 102*a*-102*e* have a corresponding adjustable support member 110. Each adjustable support member 110 of seats 102*a*-102*e* is configured to independently operate to adjust distance 168 of a corresponding seat 102, according to an exemplary embodiment. For example, adjustable support member 110 of seat 102*a* may be operated such that distance 168 of seat 102*a* relative to base 108 is ten inches, while adjustable support member 110 of seat 102*b* may be operated such that distance 168 of seat 102*b* relative to base 108 is eight inches. In this way, seats 102 may be raised or lowered independently of each other. Each of seats 102*a*-102*e* includes a control panel (e.g., a user interface, an input device, a control device, buttons, switches, levers, etc.), shown as adjustment interface 118. Adjustment interfaces 118 are each configured to adjust an operation of a corresponding adjustable support member 110. Adjustment interfaces 118 may include any number of buttons, switches, levers, dials, digital input devices, etc., configured to receive a user input and adjust an operation (e.g., a height) of a corresponding adjustable support member 110.

Base 108 has overall length 132, according to an exemplary embodiment. In some embodiments, length 132 of base 108 is less than overall length 120 of seats 102*a*-102*e*. In some embodiments, length 132 of base 108 is substantially equal to length 120 of seats 102*a*-102*e*. In some embodiments, length 132 of base 108 is greater than length 120 of seats 102*a*-102*e*. Base 108 includes horizontal central axis 136 extending through a centerpoint of base 108. Central axis 136 may be defined as being positioned at a center of length 132, according to some embodiments. In some embodiments, central axis 136 is defined as being distance 134 from a right-most surface of base 108 and distance 134 from a left-most surface of base 108. In some embodiments, each of seats 102*a*-102*e* include a corresponding central axis 126. Central axis 136 of base 108 is substantially collinear with central axis 126 of the central seat 102*c*. Base 108 defines one or more sets of apertures, holes, channels, through-holes, hollow portions, cavities, indentations, etc., shown as openings 112. Openings 112 include a first aperture 114 and a second aperture 116. In some embodiments, openings 112 are configured to facilitate transportation of seating assembly 100 by providing openings for one or more forks (e.g., forks of a pallet jack, forks of a forklift, etc.) which may be inserted into openings 112, as shown in FIGS. 4-5.

As shown in FIG. 1, base 108 includes a first set of openings, openings 112*a*, and a second set of openings, shown as openings 112*b*, according to an exemplary embodiment. Openings 112*a* and openings 112*b* are evenly spaced a distance 138 in opposite directions relative to central axis 136 of base 108. First aperture 114 and second aperture 116 of openings 112*a*/112*b* are disposed distance 130 apart, according to an exemplary embodiment. In some embodiments, distance 130 is substantially equal to a distance between forks of a floor jack, thereby facilitating transportation of seating assembly 100. In some embodiments, only one set of apertures 114/116 is defined by base 108. In some embodiments, aperture 114 and aperture 116 are spaced equally along a length of base 108 in opposite directions relative to central axis 136 of base 108. In some embodiments, openings 112a and openings 112b extend through an entire width 140 of base 108. In other embodiments, openings 112a and openings 112b extend partially through base 108.

Figure 4:
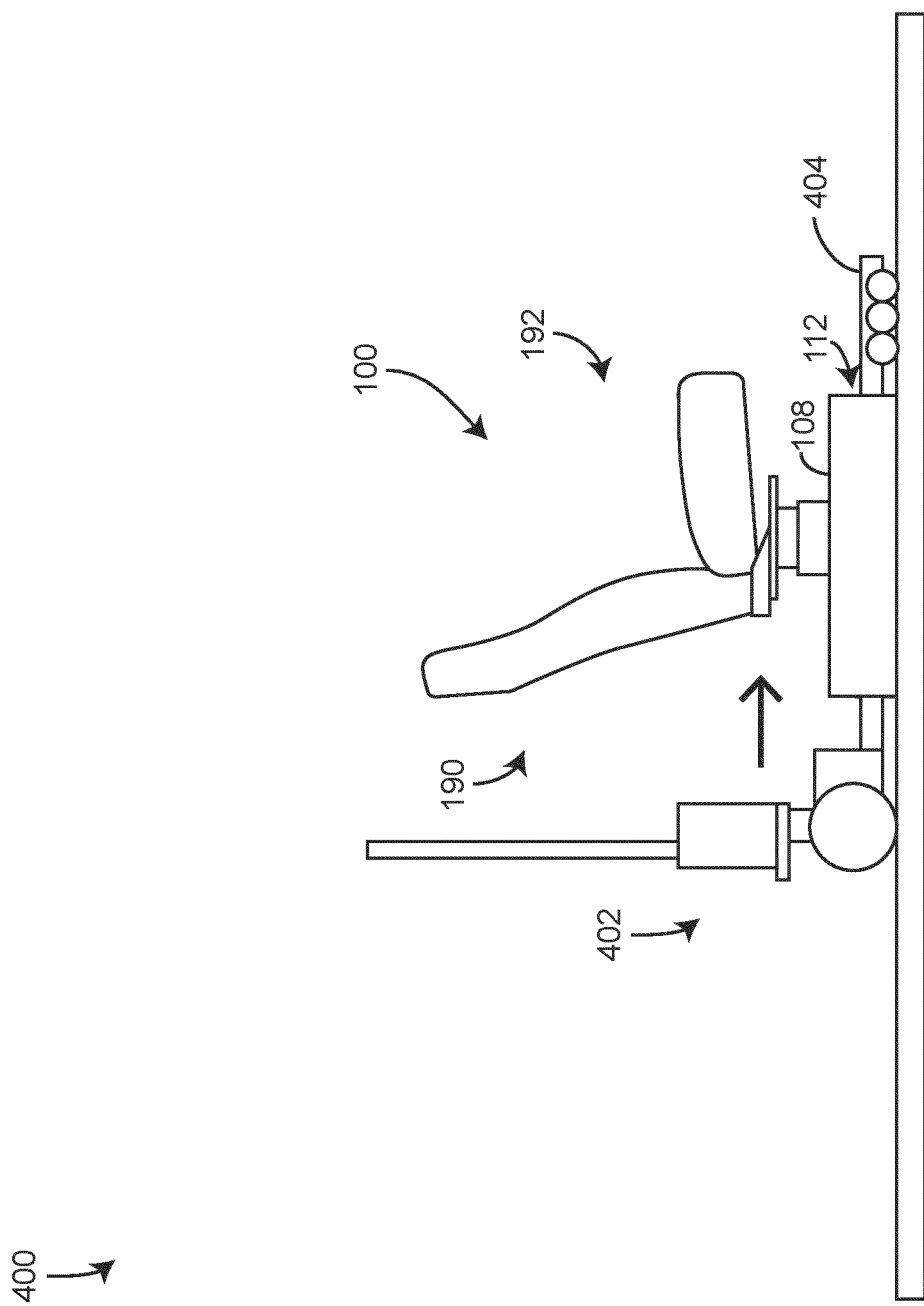
FIG. 4 is a diagram of a user transporting the seating assembly of FIG. 1, according to an exemplary embodiment.
Figure 5:
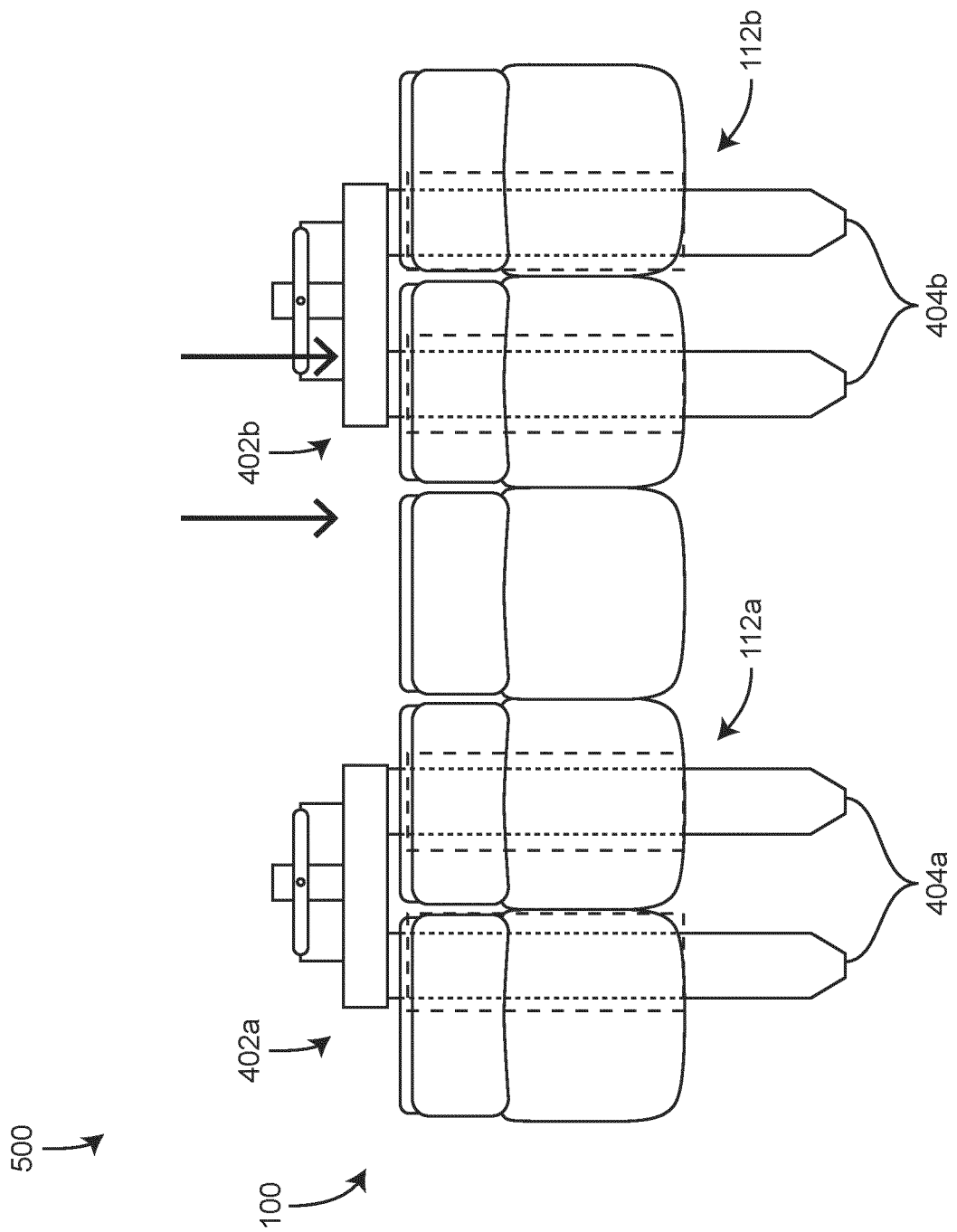
FIG. 5 is a diagram of multiple users transporting the seating assembly of FIG. 1, according to an exemplary embodiment.

As shown in diagrams 400 and 500 of FIGS. 4 and 5, openings 112 are configured to receive forks 404 of one or more transportation mechanisms 402 (e.g., a fork lift, a pallet jack), according to an exemplary embodiment. In some embodiments, a transport user may insert forks 404 into openings 112 from either back side 190 of seating assembly 100 or from front side 192 of seating assembly 100. In some embodiments, forks 404 can be inserted through the entire width 140 of base 108 (e.g., if openings 112 extend through the entire width 140 of base 108). In some embodiments, multiple transportation users may each simultaneously insert forks 404 into openings 112a and openings 112b for transportation of seating assembly 100. If seating assembly 100 is used at a sporting event (e.g., at a sporting arena), seating assembly 100 may need to be transported regularly for various events. Advantageously, openings 112 facilitate easy transportation of seating assembly 100.

Base 108 includes one or more screens (e.g., LCD screens, LED screens, display screens, frames for posters, etc.), shown as screens 162, according to an exemplary embodiment. In some embodiments, screen 162 are evenly spaced along a length of base 108. In some embodiments, screens 162 extend substantially an entire length of base 108. Screens 162 can display advertisements, athlete/player names, graphics, textual information, etc. Screens 162 may extend along substantially an entire length of base 108, or may be intermittently spaced along base 108. Screens 162 can receive a display signal or other electrical signal that provides information for graphics, scrolling imagery, scrolling text, etc. Screens 162 may use the display signal to provide the graphical, scrolling imagery, scrolling text, etc. In some embodiments, screens 162 also receive a synchronization signal so that imagery, graphics, or text that is displayed on screens 162 is synchronized with other display screens or advertisements in an environment (e.g., a sporting arena, a building, etc.) where seating assembly 100 is located. In some embodiments, multiple seating assemblies 100 are positioned adjacent, proximate, or next to each other. The graphics, imagery, text data, etc., that is displayed by screen(s) 162 across one of seating assemblies 100 may be synchronized with other graphics, imagery, text data, etc., that is displayed by screen(s) 162 across another one of seating assemblies 100. For example, if multiple seating assemblies 100 are positioned next to each other, a scrolling message, graphic, text, advertisement, etc., may continuously scroll across screen(s) 162 of multiple seating assemblies 100.

Each of seats 102a-102e include a top side 174, a bottom side 176, a rear side 172, a front side 170, a left side 180, and a right side 178, according to an exemplary embodiment. Each of seats 102a-102e include a back portion 104 and a seat portion 106. Back portion 104 includes central axis 148 extending along substantially an entire length of back portion 104. In some embodiments, central axis 148 is an average centerline of back portion 104. Seat portion 106 includes central axis 150 extending substantially an entire length of seat portion 106. In some embodiments, central axis 150 is an average centerline of seat portion 106. In some embodiment, central axis 150 is an average centerline of seat portion 106 extending along an entire length of seat portion 106. Central axis 148 and central axis 150 intersect at intersection point 160. In some embodiments, seats 102 are configured to rotate about intersection point 160 (e.g., to recline). Central axis 148 and central axis 150 define angle 152. Angle 152 represents an angle of a user's back which may be adjacent back portion 104 relative to the user's thighs which may be adjacent seat portion 106. In an exemplary embodiment, angle 152 defines an angle of a user's trunk/torso relative to the user's thighs. In some embodiments, angle 152 is greater than 90 degrees. In some embodiments, angle 152 is any value between 93 and 120 degrees. In some embodiments, angle 152 is any value between 110 degrees and 130 degrees. If angle 152 is any value between 110 and 130 degrees, both lumbar disc pressure and back muscle activity of the user is decreased. In some embodiments, angle 152 is such that seats 102 facilitate an angle of 93 to 120 degrees or 110 degrees to 130 degrees between the torso and the thigh of the one or more users while the one or more users are seated upon seats 102.

In some embodiments, back portion 104 rotates relative to seat portion 106 about intersection point 160. In some embodiments, back portion 104 rotates relative to seat portion 106 in response to a force exerted by a user. In some embodiments, a torsional spring is used at intersection point 160 to prevent excessive rotation of back portion 104. In some embodiments, as back portion 104 rotates relative to seat portion 106, angle 152 changes. In some embodiments, angle 152 between back portion 104 and seat portion 106 is fixed at a bottom threshold such that angle 152 may be greater than 90 degrees but is not less than 90 degrees. In some embodiments, both back portion 104 and seat portion 106 rotate about intersection point 160 in response to a force exerted by the user.

Seat portion 106 may include a seat pan 109, according to an exemplary embodiment. Seat pan 109 may be formed from a plastic, a foam, etc. In some embodiments, seat pan 109 is integrally formed with seat portion 106. Seat pan 109 is configured to facilitate the user's back being against (e.g., in contact with) back portion 104 while seated in seat 102.

Back portion 104 may include lumbar support 194, according to an exemplary embodiment. Lumbar support 194 may be any of one or more cushions of back portion 104, or may be a result of a profile of back portion 104. Lumbar support 194 is configured to provide support to lumbar vertebrae of the user, to facilitate proper posture of the user. Lumbar support 194 is adjustable, according to some embodiments. In an exemplary embodiment, lumbar support 194 is non-adjustable.

Figure 6:
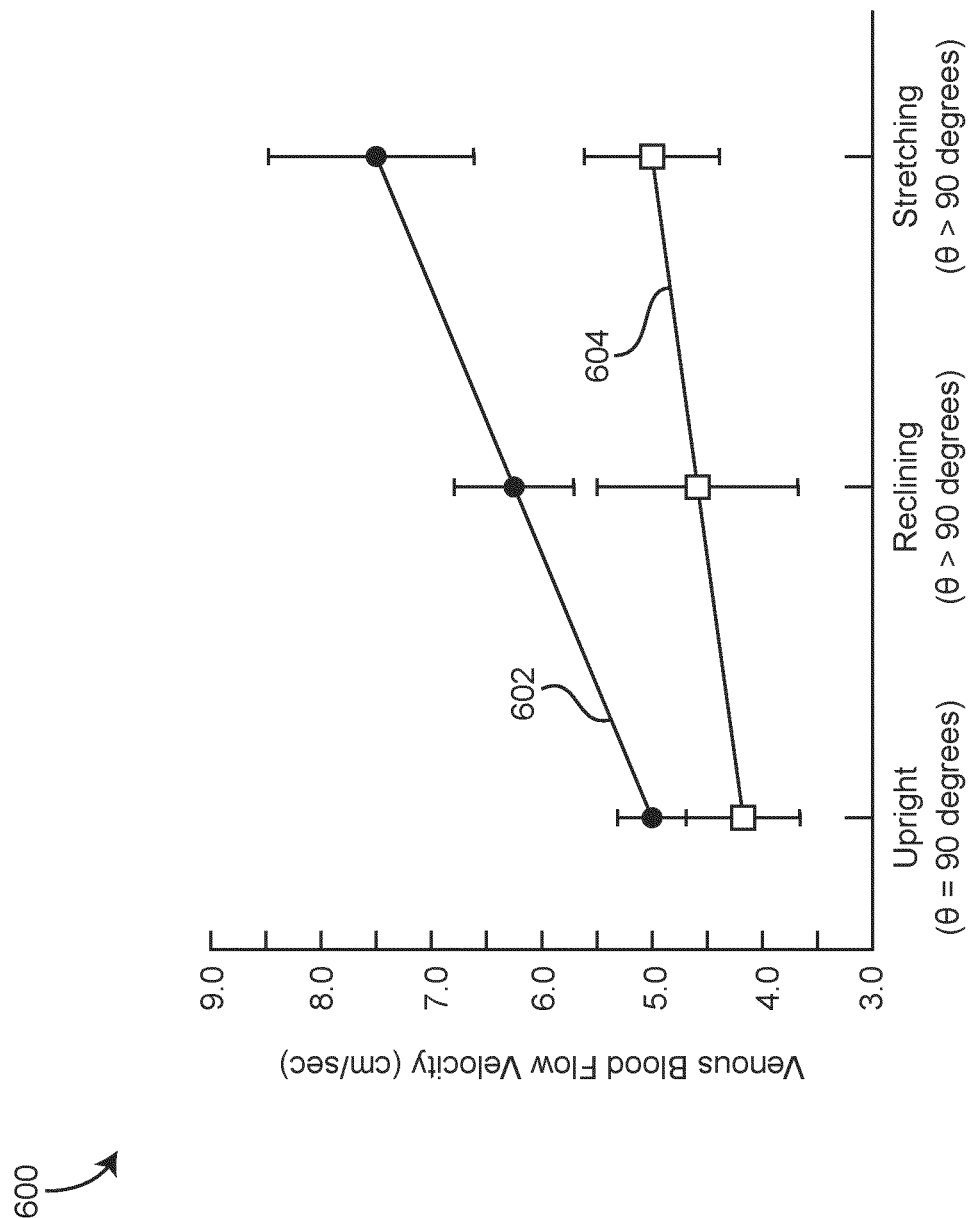
FIG. 6 is a graph illustrating a relationship between venous blood flow and incline/decline of a seated individual, according to an exemplary embodiment.
Figure 7:
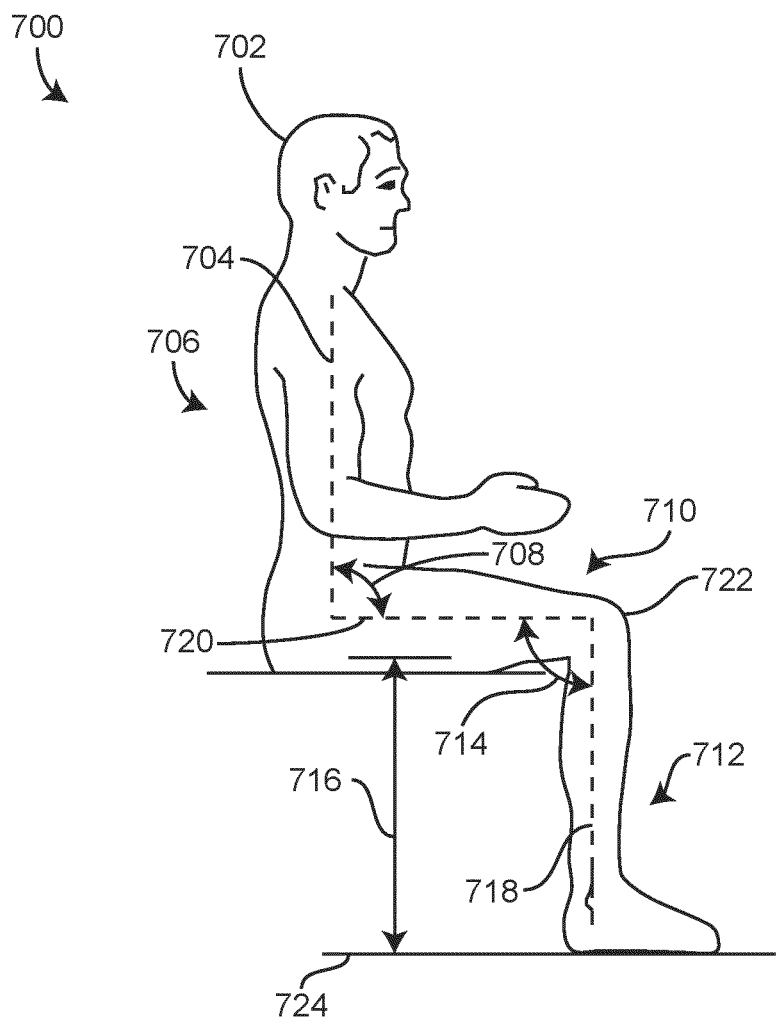
FIG. 7 is a diagram of a seated person, demonstrating a definition of various angles and popliteal height, according to an exemplary embodiment.
Figure 8:
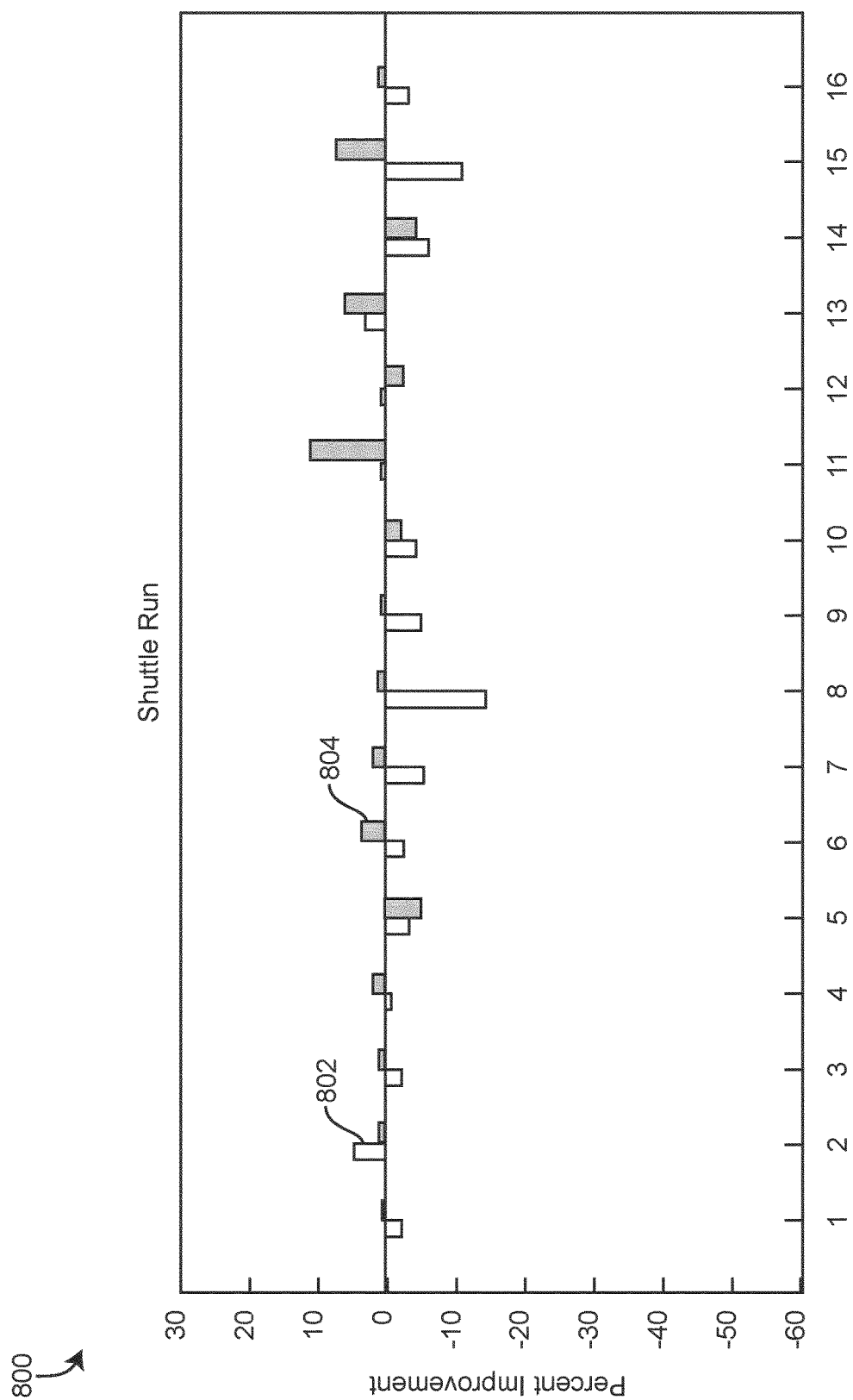
FIG. 8 is graph of test results for improvement of a shuttle run after test individuals were seated in the seating assembly of FIG. 1, as compared to a control seating assembly, according to an exemplary embodiment.
Figure 9:
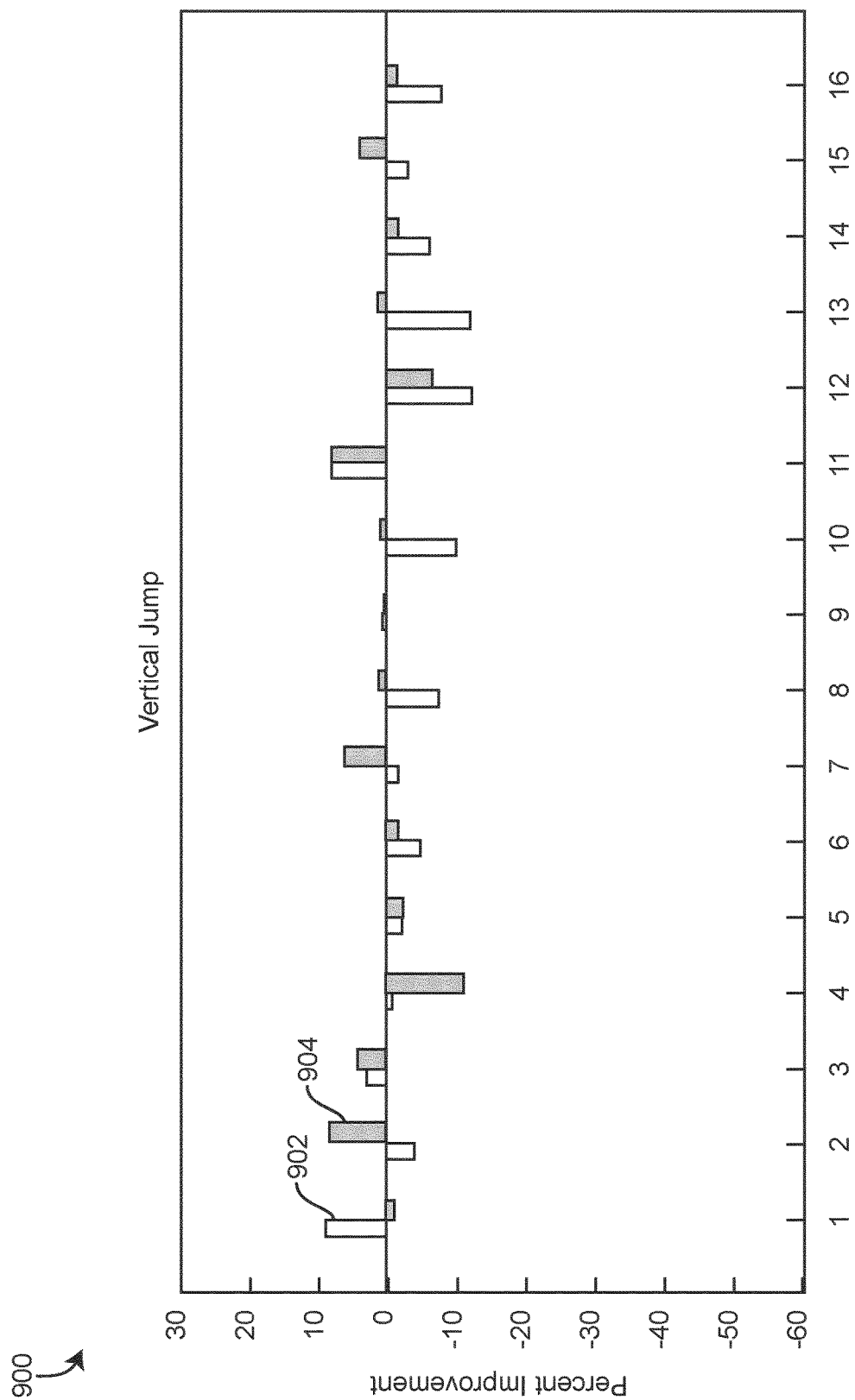
FIG. 9 is graph of test results for improvement of an average vertical jump height after test individuals were seated in the seating assembly of FIG. 1, as compared to a control seating assembly, according to an exemplary embodiment.
Figure 10:
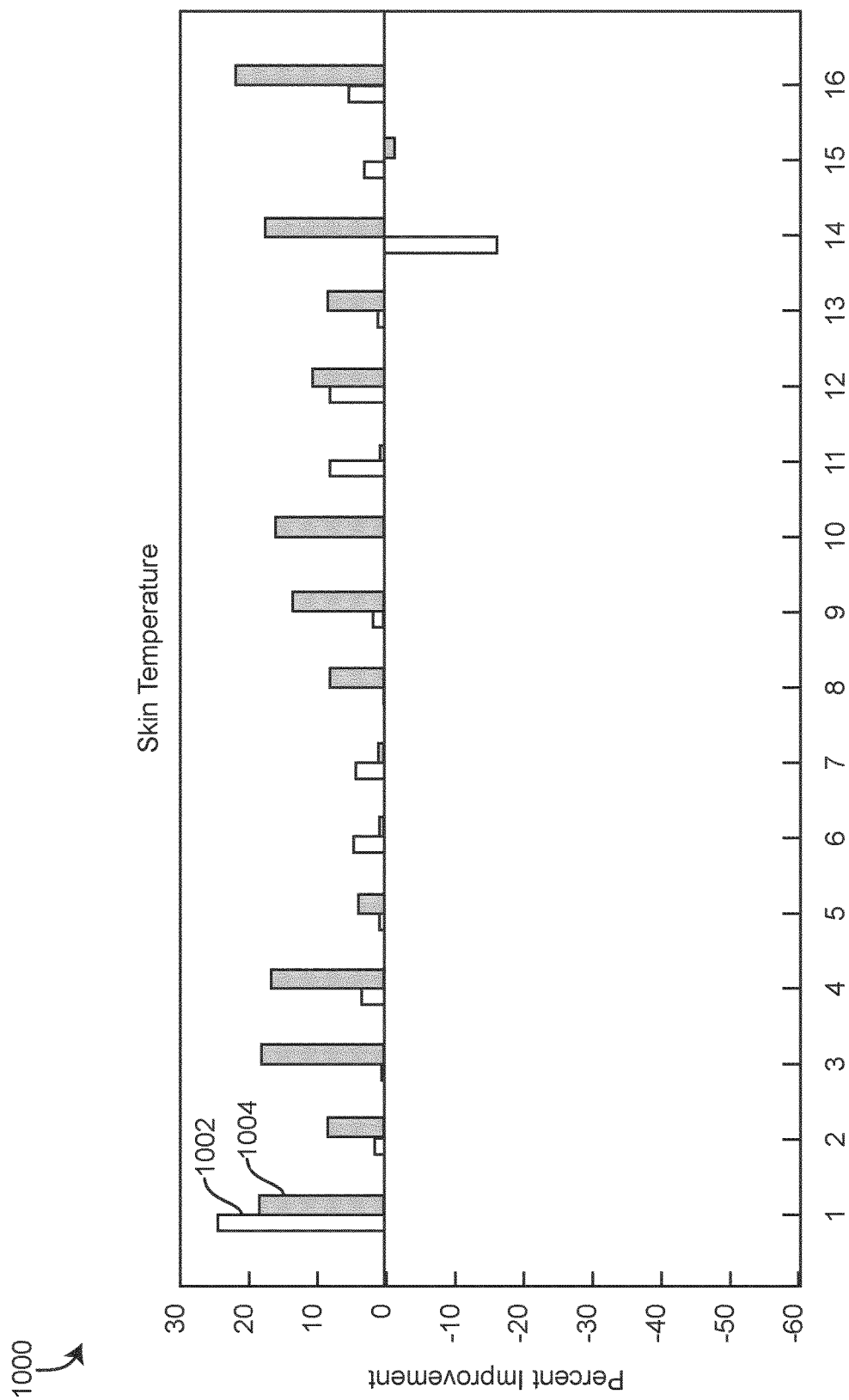
FIG. 10 is graph of test results for improvement of skin temperature after test individuals were seated in the seating assembly of FIG. 1, as compared to a control seating assembly, according to an exemplary embodiment.
Figure 11:
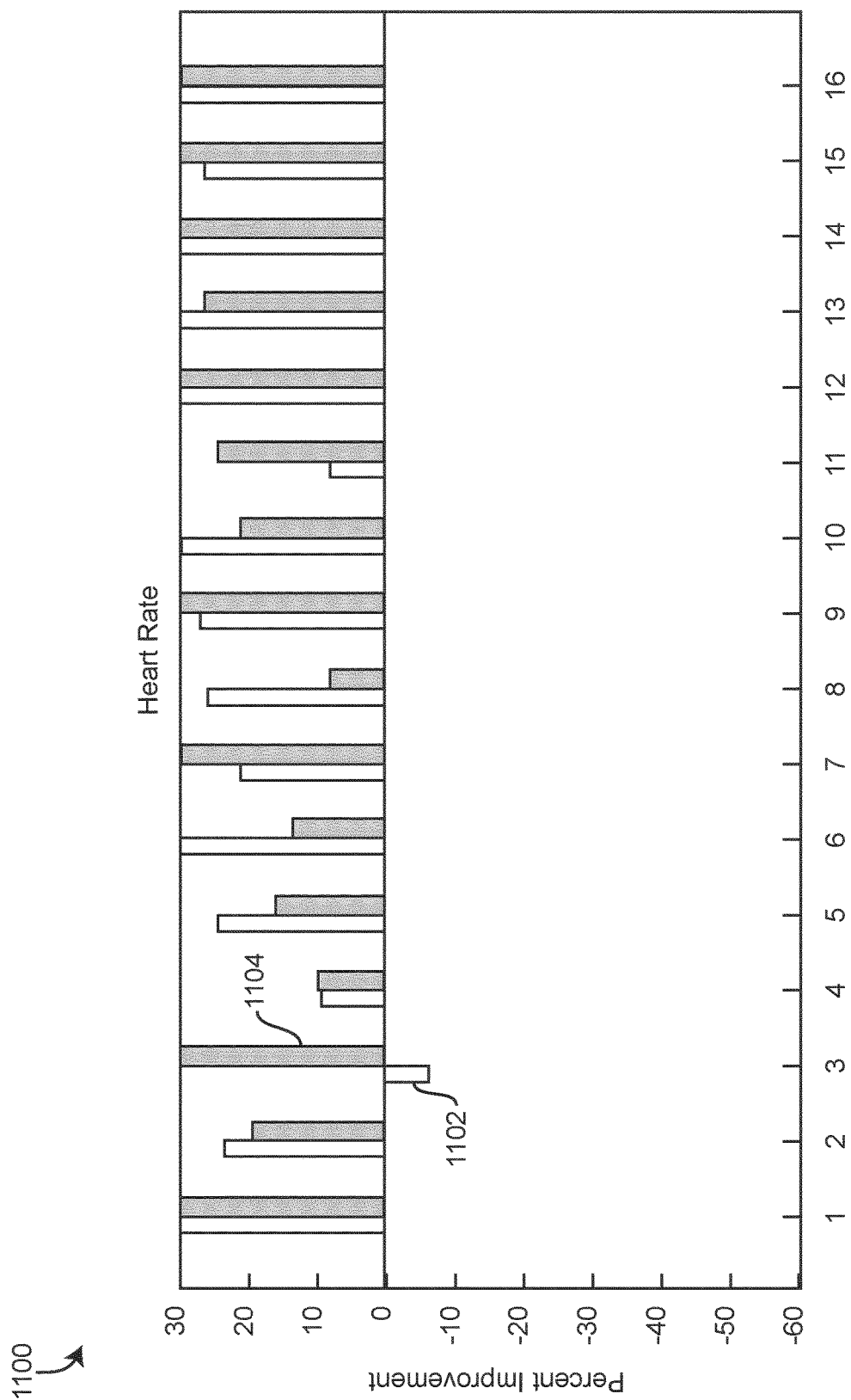
FIG. 11 is graph of test results for improvement of heart rate after test individuals were seated in the seating assembly of FIG. 1, as compared to a control seating assembly, according to an exemplary embodiment.

Referring now to FIGS. 6-7, graph 600 and diagram 700 show effects of angle 152/angle 708 (also referred to as θ) on venous blood flow to lower limbs of a user, according to some embodiments. Graph 600 includes series 602 which indicates test users breathing deeply, and series 604 which indicates test users breathing normally. For example, series 602 may indicate venous blood flow for users who were previously exercising (e.g., playing a sport). Graph 600 shows venous blood flow for increasing θ. As θ increases from 90 degrees (upright) to reclining (greater than 90 degrees), venous blood flow to the users lower limbs increases (series 604). However, the increase for users breathing deeply (series 602) is more drastic compared to the increase for users breathing normally. As users stretch (e.g., θ increases further), venous blood flow to lower limbs increases. Similarly to the change of θ from 90 degrees to greater than 90 degrees, the increase in venous blood flow for users breathing deeply (series 602) is greater than the increased venous blood flow for users breathing normally (series 604) as the users stretch (e.g., θ increases further).

As shown in FIG. 7, diagram 700 shows a user 702 seated. Angle 708 between centerline 704 of torso 706 and centerline 720 of thigh 710 (e.g., θ or a result of θ) is approximately 90 degrees. Likewise, angle 714 between centerline 720 of thigh 710 and centerline 718 of lower leg 712 (e.g., φ) is approximately 90 degrees. In some embodiments, as angle 708 (θ) increases, venous blood flow to lower limbs (i.e., thigh 710 and lower leg 712) increases, as shown in graph 600 of FIG. 6. Likewise, if angle 714 (φ) is less than 90 degrees, venous blood flow to lower leg 712 may be restricted. In some embodiments, popliteal height 716 determines angle 714. For example, if popliteal height 716 is very small, angle 714 and angle 708 may decrease, thereby restricting venous blood flow of user 702. In some embodiments, popliteal height 716 is a vertical distance between floor 724 and the crease behind knee 722 of user 702. Adjusting popliteal height 716 can be used to adjust angle 714, thereby increasing venous blood flow to lower limbs.

Referring again to FIGS. 1-5, each of adjustable support members 110 are configured to increase or decrease in height to adjust popliteal height 716 of each user, according to an exemplary embodiment. As shown in FIG. 2, distance 144 is a vertical distance between an upper and outer surface of seat portion 106 and floor 158. In some embodiments, distance 144 is or is correlated to popliteal height 716. As adjustable support member 110 increases or decreases in height (e.g., extends or retracts), distance 144 increases or decreases, thereby adjusting popliteal height 716 of the user. Adjustable support member 110 can be used to increase or decrease such that popliteal height 716 of the user is adjusted. Advantageously, a proper popliteal height 716 increases venous blood flow to lower limbs of the user.

Each seat 102 is also shown having a height 142 from floor 158, according to an exemplary embodiment. In some embodiments, height 142 is a vertical distance between floor 158 and an upper point (e.g., upper most surface) of seat 102. Height 142 may be 1011 mm. Each seat 102 is also shown having an overall depth 146. Depth 146 may be defined as a horizontal distance (e.g., parallel to floor 158) between a rear-most surface of seat 102 and a front-most surface of seat 102. Depth 146 may be 685 mm.

Referring still to FIGS. 1-5, each back portion 104 of seats 102a-102e includes a pair of heating pads 156 (e.g., heaters, heating elements, etc.), according to an exemplary embodiment. In some embodiments, heating pads 156 are resistive heating elements. Heating pads 156 may receive energy (e.g., electricity) from a power source, and dissipate heat through back portion 104. In some embodiments, heating pads 156 are positioned within back portion 104. Heating pads 156 are configured to dissipate heat through back portion 104. In some embodiments, heating pads 156 dissipate heat such that a surface temperature of back portion 104 is approximately 110 degrees Fahrenheit or between 110 and 100 degrees Fahrenheit (a high heating mode). In some embodiments, heating pads 156 and/or heating pads 164 dissipate heat at 40 degrees Celsius or 106 degrees Fahrenheit. In some embodiments, heating pads 156 and/or heating pads 154 dissipate heat at any value between 38 and 45 degrees Celsius. In some embodiments, heating pads 156 and/or heating pads 154 dissipating heat at a value between 38 and 45 degrees Celsius facilitates maintaining muscle temperature of a user and facilitates increased blood flow. Advantageously, maintaining muscle temperature and facilitating increased blood flow may improve athletic performance of the user. In some embodiments, heating pads 156 dissipate heat such that a surface temperature of back portion 104 is between 85 and 100 degrees Fahrenheit (a medium heating mode). In some embodiments, heating pads 156 dissipate heat such that a surface temperature of back portion 104 is between 75 and 85 degrees Fahrenheit (a low heating mode). Advantageously, as a user sits on seat 102, heat dissipated by heating pads 156 is absorbed by the torso (e.g., torso 706) of the user. This facilitates venous blood flow of the user at heated regions of the user. In some embodiments, heating pads 156 extend through substantially an entire length of back portion 104. In some embodiments, only one heating pad 156 is configured to dissipate heat through back portion 104.

Heating pads 154 and heating pads 156 may be operated independently of each other, or independently across seats 102. For example, a first seat may provide heat at a first rate through heating pads 154 and heating pads 156, while a second seat may provide heat at a second rate through heating pads 154 and heating pads 156. In some embodiments, the heating pads 154 and heating pads 156 of a single seat are configured to provide a same or uniform amount of heat. In some embodiments, heating pads 154 and heating pads 156 are independently operable, controllable, etc., to provide differing amounts of heat to the user's torso or lower limbs. It should be understood that the heating provided to the user's torso or lower limbs by heating pads 154 and heating pads 156 may be independently operated at each seat 102 so that seats 102 independently provide differing amounts of heat, depending on a user's preference.

Each back portion 104 includes a back cushion (e.g., a pad, a foam piece, etc.), shown as back cushion 196. In some embodiments, heating pads 156 are positioned within back cushion 196. In some embodiments, back cushion 196 is or includes multiple cushions. Back cushion 196 is positioned within back portion liner 200, according to an exemplary embodiment. In some embodiments, heating pads 156 are positioned within back portion liner 200 directly adjacent back cushion 196 (e.g., adjacent a front facing surface of back cushion 196). Back portion liner 200 may be any of leather, canvas, polyester, polypropylene, nylon, acrylic, olefin, etc. In some embodiments, back portion liner 200 is configured to cover substantially an entire surface area of back cushion 196.

Referring still to FIGS. 1-5, each seat portion 106 of seats 102a-103e includes heating pads 164 (e.g., heaters, heating elements, etc.), according to an exemplary embodiment. Heating pads 164 may be the same type of heating pads as heating pads 156 of back portion 104. Heating pads 164 may be positioned within seat portion 106 and configured to dissipate heat through seat portion 106 to provide the dissipated heat to a user. Heating pads 164 may be configured to operate similarly to heating pads 156 (e.g., in a high heating mode, a medium heating mode, and a low heating mode, etc.). Advantageously, the heat dissipated by heating pads 164 may be provided through seat portion 106 to lower limbs (e.g., thighs and lower legs) of a user. The heat received by the lower limbs of the user facilitate venous blood flow through the lower limbs of the user.

Each seat portion 106 includes a seat cushion (e.g., a pad, a foam piece, etc.), shown as seat cushion 198. In some embodiments, heating pads 164 are positioned within seat cushion 198. In some embodiments, seat cushion 198 is or includes multiple cushions. Seat cushion 198 is positioned within seat portion liner 202, according to an exemplary embodiment. In some embodiments, heating pads 164 are positioned within seat portion liner 202 directly adjacent seat cushion 198 (e.g., adjacent a front facing surface of seat cushion 198). Seat portion liner 202 may be any of leather, canvas, polyester, polypropylene, nylon, acrylic, olefin, etc. In some embodiments, seat portion liner 202 is configured to cover substantially an entire surface area of seat cushion 198.

Adjustment interfaces 118 are configured to individually adjust at least one of an amount or rate of heat dissipated by heating pads 164 and/or heating pads 164 of a corresponding seat 102, according to an exemplary embodiment. For example, the user may provide an input at adjustment interface 118 to operate heating pads 156 in a high heating mode, an input at adjustment interface 118 to operate heating pads 164 at a medium heating mode, an input at adjustment interface 118 to operate heating pads 164 at a low heating mode, etc. In some embodiments, adjustment interface 118 is configured to receive a temperature setpoint for each of back portion 104 (e.g., a temperature setpoint for heating pads 156) and seat portion 106 (e.g., a temperature setpoint for heating pads 164). In some embodiments, each of seats 102a-102e includes a corresponding adjustment interface 118, configured to adjust a temperature (e.g., a surface temperature) of any of heating pads 156 and heating pads 164 for the particular seat 102.

Seat and Back

Figure 13:
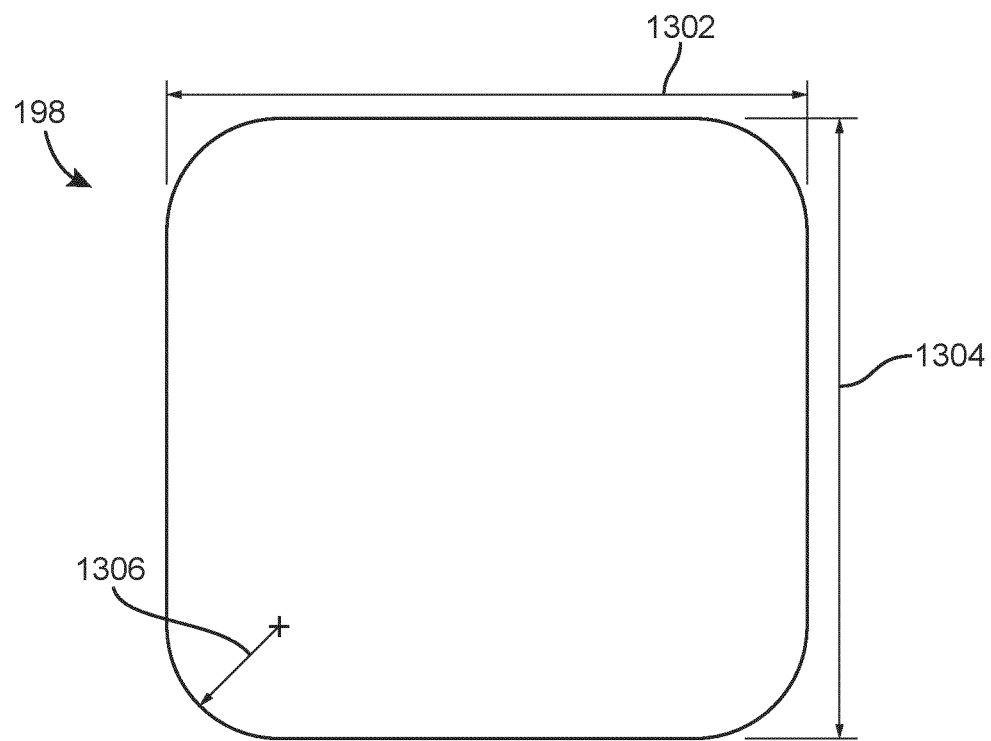
FIG. 13 is a top view of a seat cushion of the seating assembly of FIG. 1, according to an exemplary embodiment.
Figure 14:
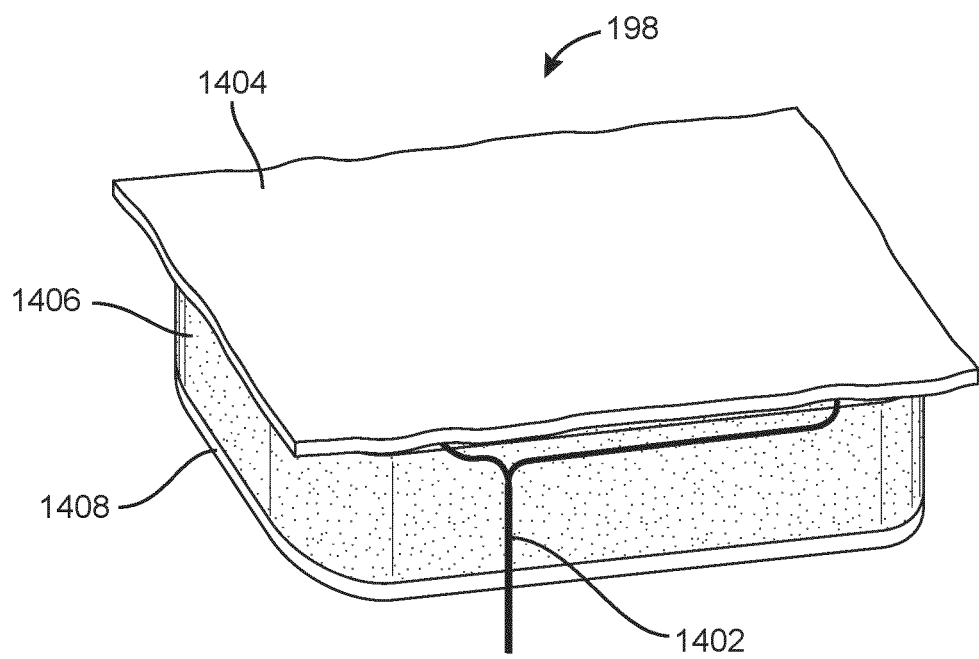
FIG. 14 is a perspective view of a seat cushion of the seating assembly of FIG. 1, according to an exemplary embodiment.
Figure 15:
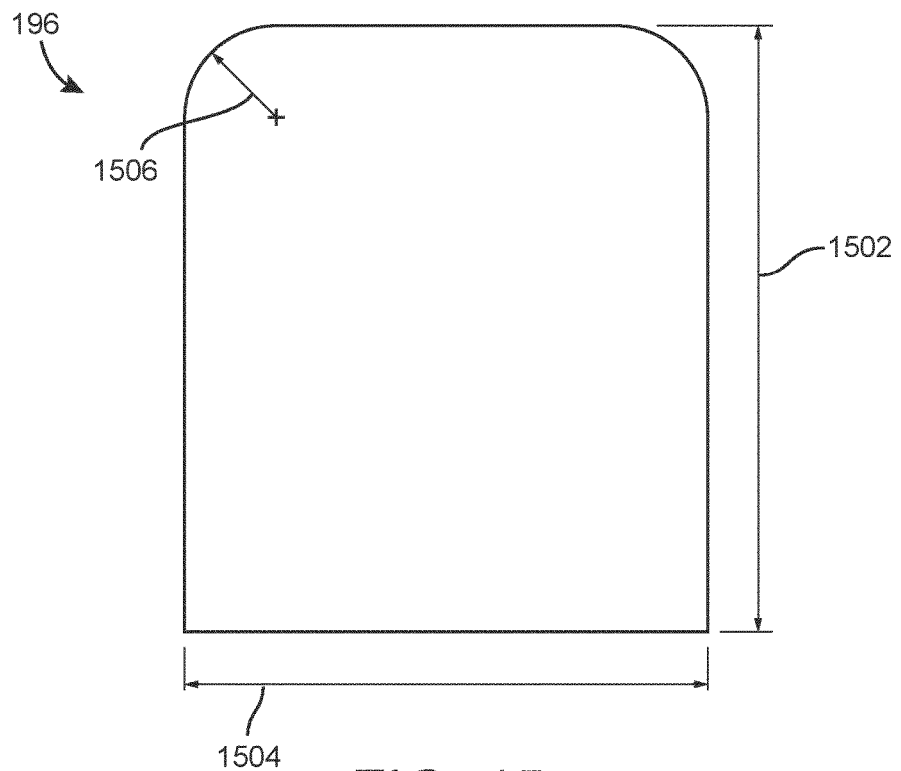
FIG. 15 is a top view of a back cushion of the seating assembly of FIG. 1, according to an exemplary embodiment.
Figure 16:
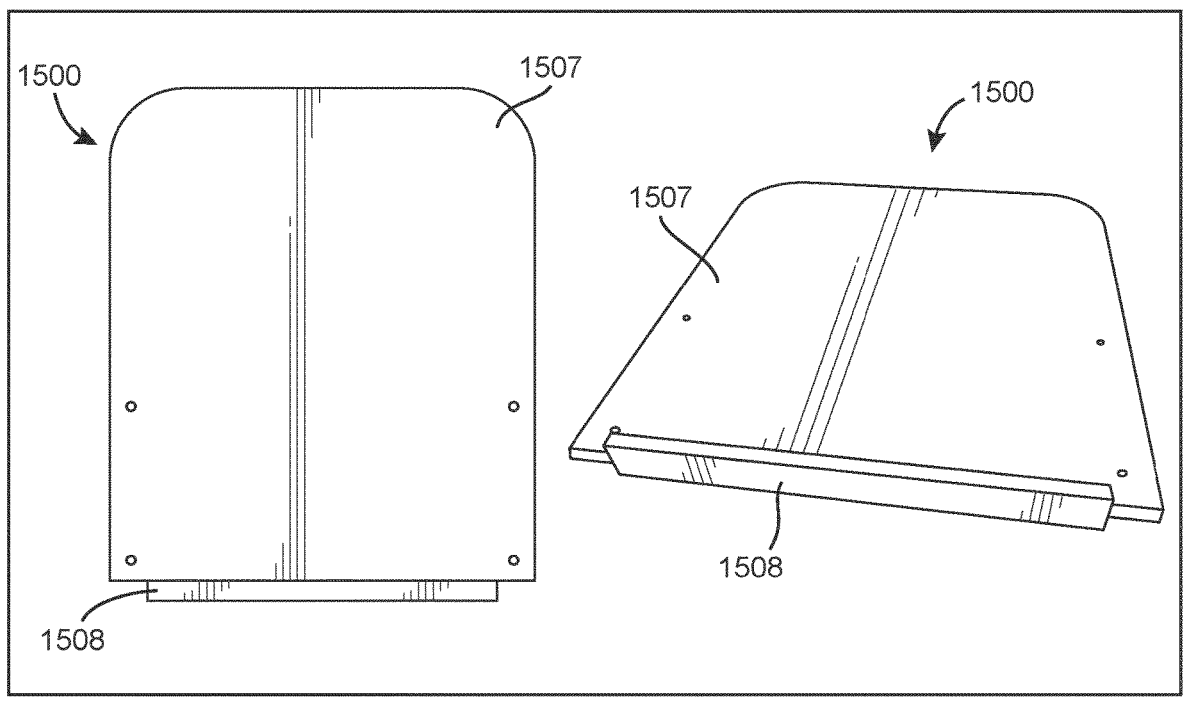
FIG. 16 is a perspective view of a back cushion of the seating assembly of FIG. 1, according to an exemplary embodiment.
Figure 17:
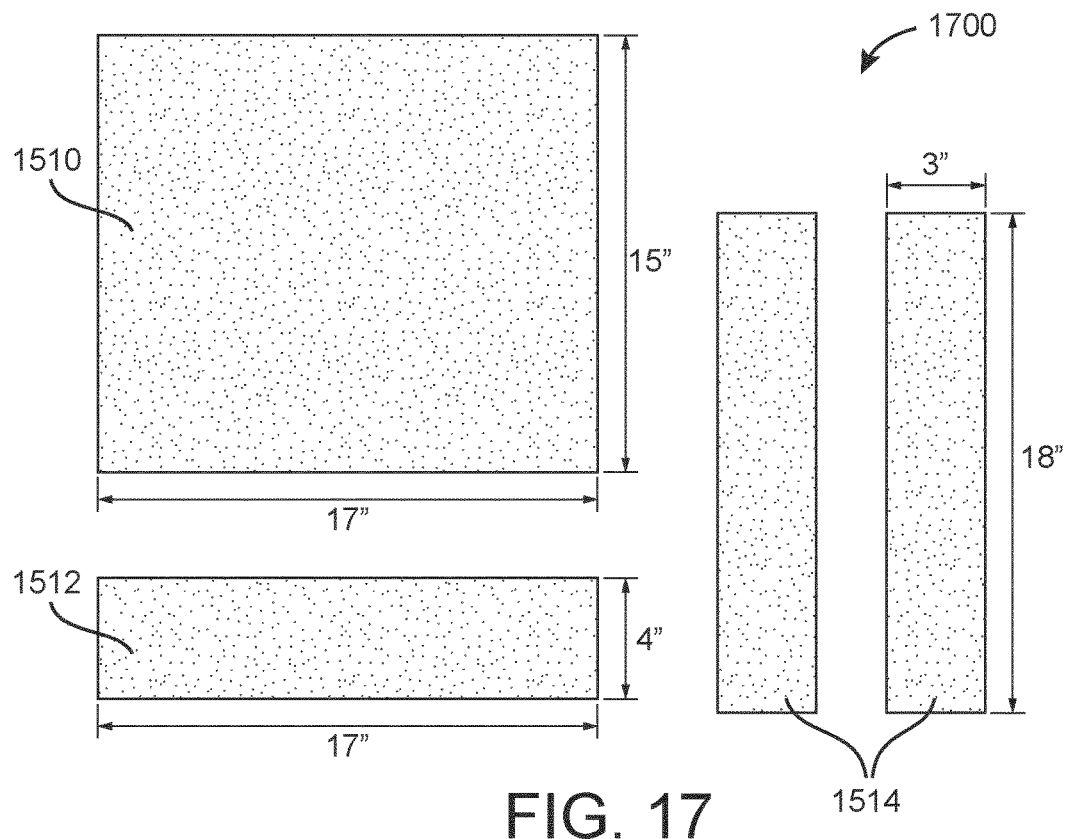
FIG. 17 is a perspective view of foam pieces of a back cushion of the seating assembly of FIG. 1, according to an exemplary embodiment.

Referring now to FIGS. 13-14, seat cushion 198 is shown in greater detail, according to an exemplary embodiment. Seat cushion 198 has a generally square or rectangular shape with rounded corners. Seat cushion 198 has a height 1302 and a length 1304. In some embodiments, height 1302 is equal to length 1304, while in other embodiments, height 1302 is greater than or less than length 1304. In an exemplary embodiment, height 1302 is equal to length 1304 and is 18 inches. Each of the four corners of seat cushion 198 are shown rounded. In an exemplary embodiment, radius 1306 of the round of each corner is 3 inches. In an exemplary embodiment, seat cushion 198 is 3 inches thick.

Seat cushion 198 includes a foam piece 1406 and an insulation piece 1404. In an exemplary embodiment, foam piece 1406 is a high-density polyurethane foam and insulation piece 1404 is Dacron insulation. In some embodiments, heating pads 164 are positioned between foam piece 1406 and insulation piece 1404. In other embodiments, heating pads 164 are installed on an exterior surface of foam piece 1406. In some embodiments, heating pads 164 cover an entire exterior surface of foam piece 1406 (e.g., an entire front surface, an entire rear surface).

In some embodiments, seat cushion 198 is connected (e.g., adhered, upholstered, riveted, etc.) to a rigid support member, shown as rigid member 1408. Rigid member 1408 may have the same profile as seat cushion 198. In an exemplary embodiment, rigid member 1408 is made from wood.

Referring now to FIGS. 15-18, back cushion 196 is shown in greater detail, according to an exemplary embodiment. Back cushion 196 is an overall rectangular shape having height 1502 and length 1504. In an exemplary embodiment, height 1502 is 19 inches and length 1504 is 17 inches. Back cushion 196 is shown to include two rounded corners. In some embodiments, the upper two corners of back cushion 196 are rounded. In other embodiments, all four corners of back cushion 196 are rounded. In an exemplary embodiment, the rounds have a radius 1506 of 3 inches.

In some embodiments, back cushion 196 is attached to a seat back 1500. Seat back 1500 may have a same general shape as back cushion 196 (e.g., generally rectangular, same or similar dimensions, etc.). Seat back 1500 includes a generally planar rigid member, shown as rigid member 1507. In an exemplary embodiment, rigid member 1507 has a same profile as back cushion 196. In some embodiments, seat back 1500 includes an upholstery member, shown as upholstery support piece 1508. In some embodiments, upholstery support piece 1508 runs along a perimeter of rigid member 1507. In other embodiments, upholstery support piece 1508 runs along one or more edges of a perimeter of rigid member 1507. In an exemplary embodiment, both rigid member 1507 and upholstery support piece 1508 are made from wood. In other embodiments, rigid member 1507 is made from steel, aluminum, or any other material which provides sufficient structural strength.

Back cushion 196 may be connected to seat back 1500. In an exemplary embodiment, back cushion 196 is adhered to seat back 1500. In other embodiments, back cushion 196 is upholstered to seat back 1500. In some embodiments, back cushion 196 is both adhered to seat back 1500 and upholstered to seat back 1500 (e.g., both glued and riveted).

Figure 18:
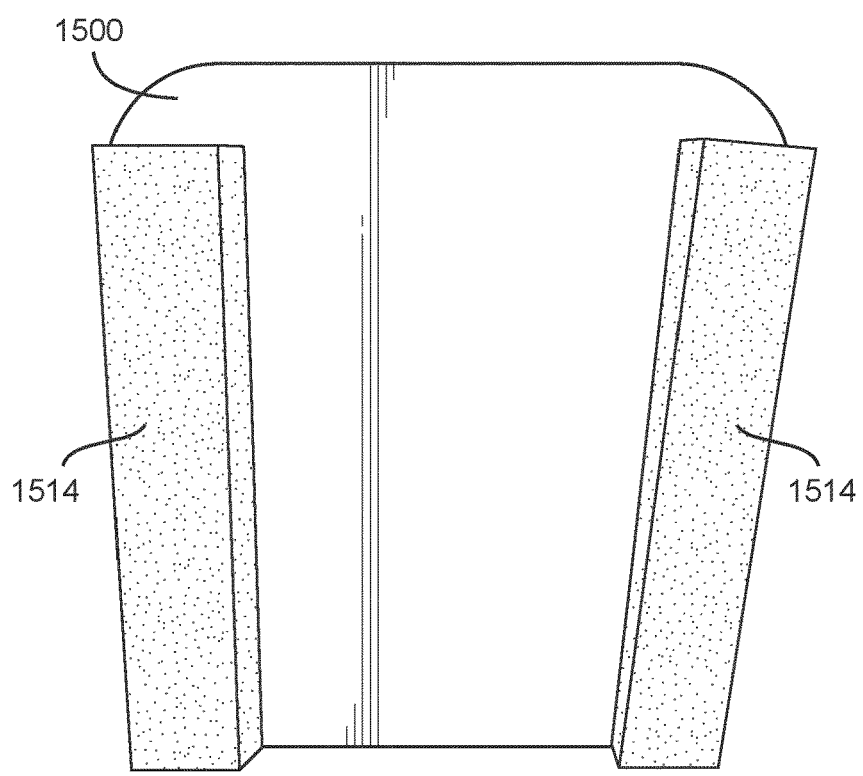
FIG. 18 is a perspective view of foam pieces of a back cushion of the seating assembly of FIG. 1 adhered to a seat back, according to an exemplary embodiment.

Back cushion 196 may include a foam piece 1700. In some embodiments, foam piece 1700 has a same profile, shape, perimeter, area, etc. as back cushion 196. Foam piece 1700 may be made of a medium-density polyurethane foam. In some embodiments, heating pads 156 are installed below a surface of foam piece 1700. In some embodiments, foam piece 1700 includes a first rectangular piece 1510, a second rectangular piece 1512, and two third rectangular pieces 1514. First rectangular piece 1510, second rectangular piece 1512 and the two third rectangular pieces 1514 are all three inches thick. First rectangular piece 1510 has a length of 17 inches and a height of 15 inches, according to an exemplary embodiment. Second rectangular piece 1512 has a length of 17 inches and a height of 4 inches. Rectangular pieces 1514 have a length of 3 inches and a height of 18 inches. Any of first rectangular piece 1510, second rectangular piece 1512 and third rectangular pieces 1514 may be adhered to a surface of seat back 1500 as shown in FIG. 18.

Figure 29:
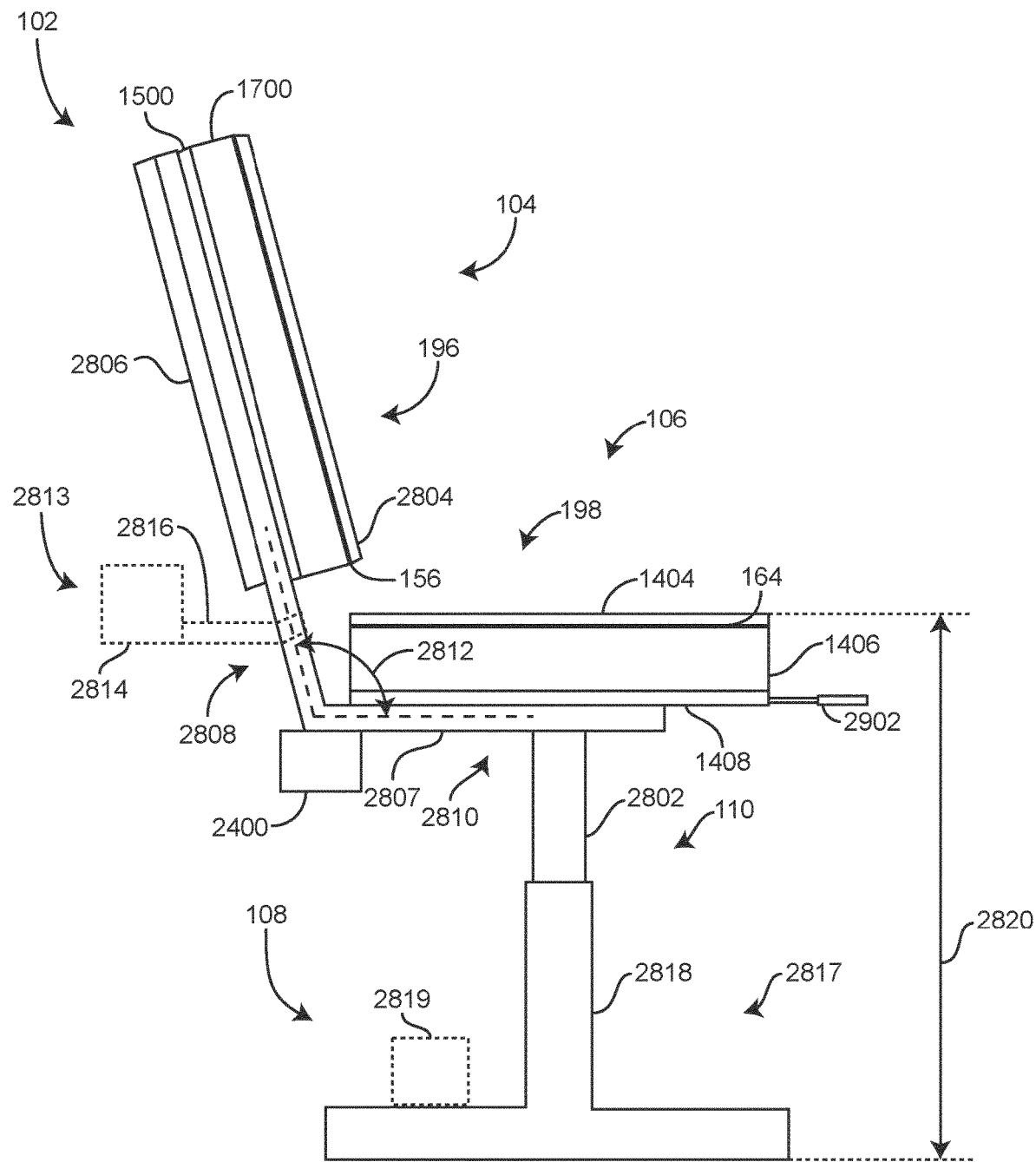
FIG. 29 is a schematic illustrating an electrical system of the heating elements of the seating assembly of FIG. 1, according to an exemplary embodiment.
Figure 30:
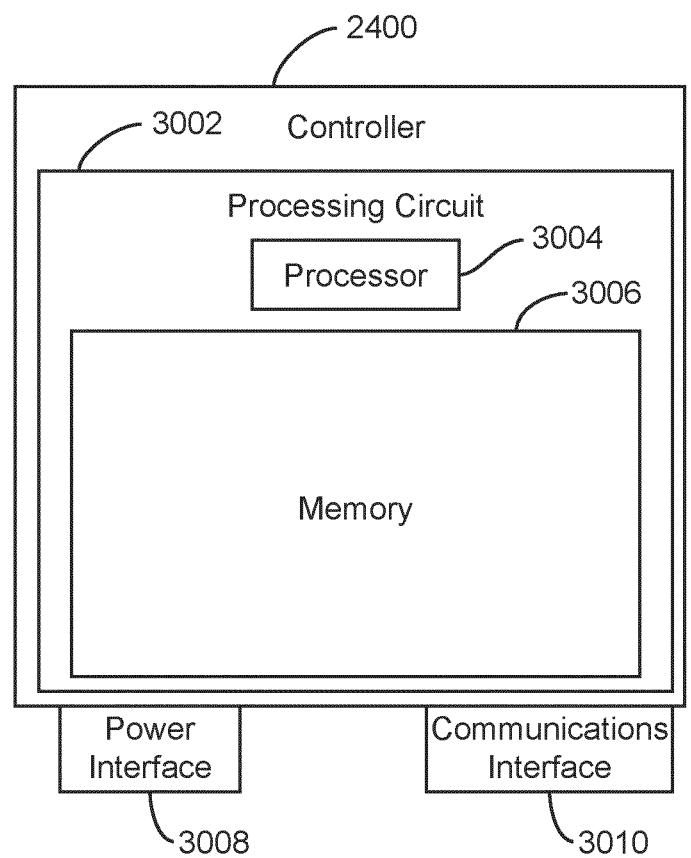
FIG. 30 is a block diagram of a controller of the seating assembly of FIG. 1, according to an exemplary embodiment.

Referring now to FIG. 29, a side sectional view of one of seats 102 is shown, according to an exemplary embodiment. Seat 102 includes a seat frame 2807 coupled to adjustable support member 110, back portion 104 and seat portion 106. Seat portion 106 includes seat cushion 198 connected to seat frame lower portion 2810. Back portion 104 includes back cushion 196 connected to seat frame upper portion 2808. Seat frame lower portion 2810 is coupled (e.g., removably, fixedly, etc.) to movable member 2802 of adjustable support member 110.

Seat frame lower portion 2810 and seat frame upper portion 2808 form angle 2812, according to an exemplary embodiment. Angle 2812 may be greater than 90 degrees. In an exemplary embodiment, angle 2812 is 105 degrees. In other embodiments, angle 2812 is 115 degrees. In other embodiments, angle 2812 is between 110 and 120 degrees. Angle 2812 may be the same as or related to angle 152 and/or angle 708.

Seat cushion 198 includes insulation piece 1404, heating pads 164, foam piece 1406, and rigid member 1408, according to an exemplary embodiment. Rigid member 1408 is coupled to seat frame lower portion 2810. Foam piece 1406 is adhered and/or coupled (e.g., riveted) to rigid member 1408. Heating pads 164 are disposed between insulation piece 1404 and foam piece 1406. In some embodiments, heating pads 164 are disposed within (e.g., sub-flush) foam piece 1406. For example, foam piece 1406 may include one or more apertures (e.g., rectangular apertures) defining an inner volume configured to receive heating pads 164. In some embodiments, an additional foam piece is disposed between heating pads 164 and insulation piece 1404. In some embodiments, an additional foam piece is disposed at an exterior surface of insulation piece 1404. In some embodiments, the additional foam piece disposed at the exterior surface of insulation piece 1404 has a same profile (e.g., area, shape, perimeter, etc.) as foam piece 1406 but is thinner (e.g., less thick, 2 inches in thickness, 1 inch in thickness, etc.) than foam piece 1406.

Back cushion 196 includes seat back 1500, foam piece 1700, heating pads 156, and an insulation piece 2804. In an exemplary embodiment, seat back 1500 is connected to seat frame upper portion 2808 (e.g., removably, fixedly, with fasteners, etc.). Foam piece 1700 is adhered and/or coupled to seat back 1500 (e.g., via a glue and/or rivets). Heating pads 156 are disposed between insulation piece 2804 and foam piece 1700. In an exemplary embodiment, insulation piece 2804 has a same profile as back cushion 196 and is manufactured from a same material as insulation piece 1404. In some embodiments, back cushion 196 includes a back foam piece 2806. Back foam piece 2806 may be configured to provide cushioning so that seat frame upper portion 2808 does not protrude outwards from back side 190 of seating assembly 100. In some embodiments, back foam piece 2806 is made from a high density or medium density polyurethane foam. In some embodiments, heating pads 156 are configured similarly to heating pads 164. For example, an additional foam piece may be positioned at an exterior surface of insulation piece 2804, or heating pads 156 may be positioned within an aperture defining an inner volume of foam piece 1700.

In some embodiments, seat 102 includes a storage member (e.g., a container, a shelf, etc.), shown as water bottle holder 2813. In some embodiments, water bottle holder 2813 is coupled (e.g., removably, fixedly, etc.) to seat frame upper portion 2808. In other embodiments, water bottle holder 2813 is coupled to seat frame lower portion 2810. Water bottle holder 2813 includes a support member 2816 and a containing member 2814. Support member 2816 is coupled to seat frame upper portion 2808 (or seat frame lower portion 2810) and produces a distance outward from seat frame upper portion 2808. Containing member 2814 is configured to hold, secure, grasp, contain, etc., one or more items and is connected to support member 2816.

In an exemplary embodiment, back portion 104 and seat portion 106 are covered with a vinyl, leather, or polyester covering. In some embodiments, the covering surrounds all exterior surfaces of back portion 104 and seat portion 106. The coverings may wrap around back portion 104 and seat portion 106 and be connected (e.g., by rivets, screws, etc.) to any of back foam piece 2806, rigid member 1408, and seat back 1500. In some embodiments, the covering is water proof such that perspiration from a user does not soak into seat cushion 198 and/or back cushion 196.

Seat Frame

Figure 22:
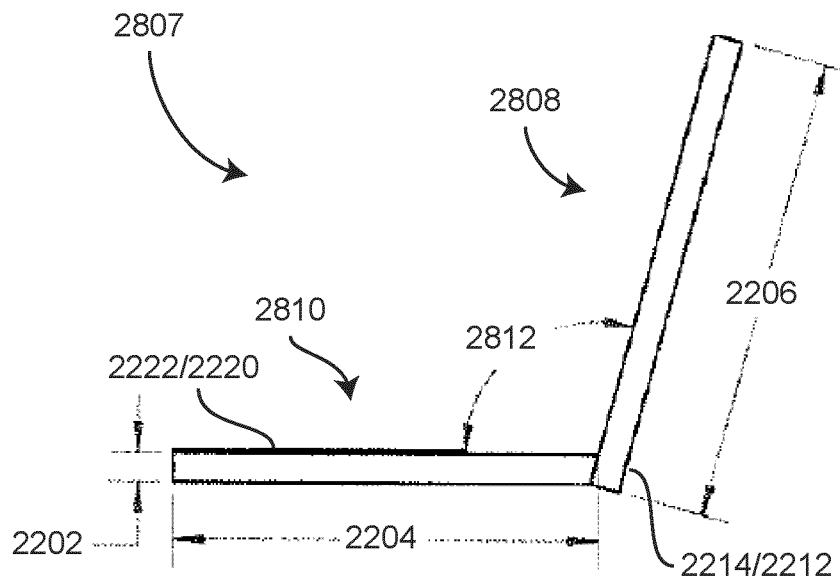
FIG. 22 is a side view of a seat frame of the seating assembly of FIG. 1, according to an exemplary embodiment.
Figure 23:
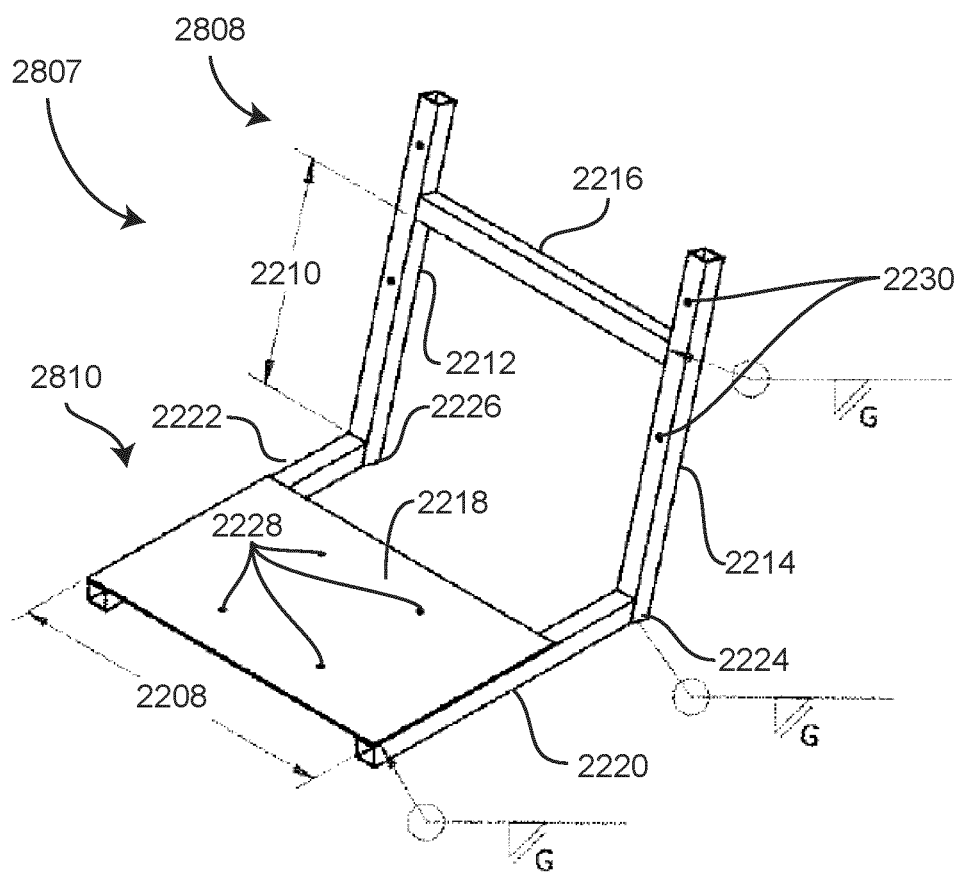
FIG. 23 is a perspective view of a seat frame of the seating assembly of FIG. 1, according to an exemplary embodiment.

Referring now to FIGS. 22-23, seat frame 2807 is shown in greater detail, according to an exemplary embodiment. Seat frame 2807 includes seat frame upper portion 2808 and seat frame lower portion 2810. Seat frame upper portion 2808 and seat frame lower portion 2810 define angle 2812. In an exemplary embodiment, angle 2812 is 105 degrees. In other embodiments, angle 2812 is 115 degrees. In other embodiments, angle 2812 is between 110 and 120 degrees. Seat frame upper portion 2808 includes upper frame members (e.g., bars, beams, etc.), shown as upper tubular members 2212 and 2214. Seat frame lower portion 2810 includes lower frame members (e.g., bars, beams, etc.), shown as lower tubular member 2222 and 2220. Seat frame upper portion 2808 includes a cross member, shown as cross tubular member 2216. Cross tubular member 2216 extends between upper tubular member 2212 and upper tubular member 2214. Cross tubular member 2216 provides structural support for upper tubular member 2212 and upper tubular member 2214. Upper tubular member 2214 and upper tubular member 2212 are disposed a distance 2208 apart. In an exemplary embodiment, distance 2208 is 16 inches. In an exemplary embodiment, upper tubular member 2214 and upper tubular member 2212 are parallel and have a same profile. Upper tubular members 2214 and 2212 are connected to lower tubular members 2220 and 2222 at corners 2224 and 2226, respectively. In an exemplary embodiment, cross tubular member 2216 is disposed a distance 2210 from corners 2224/2226 along a centerline of either upper tubular member 2212 or upper tubular member 2214. In an exemplary embodiment, distance 2210 is 10 inches. Upper tubular members 2212/2214 have an overall length 2206. In an exemplary embodiment, overall length 2206 is 16 inches.

Seat frame lower portion 2810 includes lower tubular member 2222 and lower tubular member 2220, according to an exemplary embodiment. Lower tubular member 2222 and lower tubular member 2220 are disposed distance 2208 apart. Lower tubular member 2222 and lower tubular member 2220 have an overall length 2204. In an exemplary embodiment, length 2204 is 14.5 inches. Seat frame lower portion 2810 includes a support plate shown as support member 2218, according to an exemplary embodiment. Support member 2218 rests upon a top surface of lower tubular member 2220 and 2222 and extends between lower tubular member 2222 and 2220. Support member 2218 is configured to provide a surface for a user to sit upon and a surface to connect to rigid member 2408. In an exemplary embodiment, support member 2218 includes one or more connection interfaces 2228 configured to facilitate connection between rigid member 2408 and seat frame 2807. Likewise, upper tubular members 2214 and 2212 include one or more connection interface 2230 to facilitate connection between seat back 1500 and seat frame 2807. In some embodiments, support member 2218 is a steel plate. In an exemplary embodiment, support member 2218 is a 7 inch by 16-inch steel plate. Any of the connections (e.g., between cross tubular member 2216 and upper tubular members 2214/2212 and/or between upper tubular members 2214/2212 and lower tubular members 2220/2222 and/or between support member 2218 and lower tubular members 2220/2222) are welded connections.

In an exemplary embodiment, upper tubular members 2214/2212 and lower tubular members 2220/2222 are generally square steel tubing. In some embodiments, upper tubular members 2214/2212 and lower tubular members 2220/2222 are straight steel members having an internal volume extending through an entire length. In other embodiments, upper tubular members 2214/2212 and lower tubular members 2220/2222 are square steel tubular members. In other embodiments, upper tubular members 2214/2212 and lower tubular members 2220/2222 are square steel tubular members having rounded corners. In an exemplary embodiment, upper tubular members 2214/2212 and lower tubular members 2220/2222 are 1 inch by 1-inch square steel tubing.

Support Frame

Figure 19:
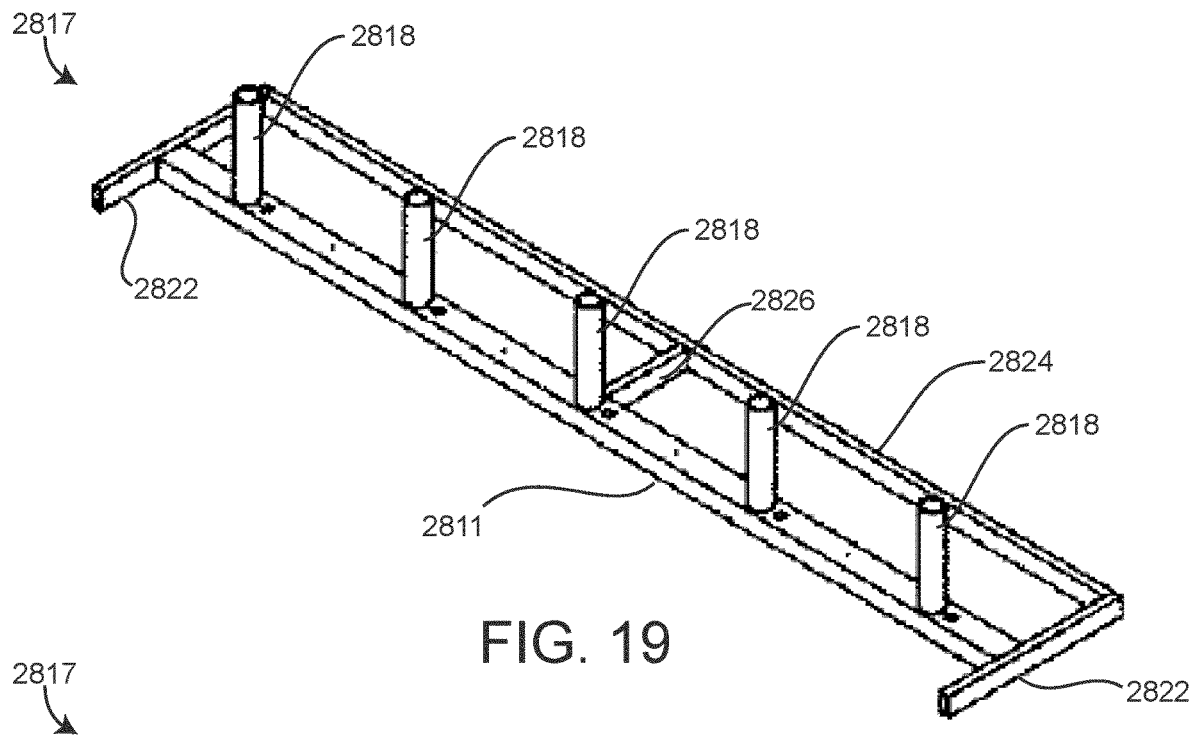
FIG. 19 is a perspective view of a base frame of the seating assembly of FIG. 1, according to an exemplary embodiment.
Figure 20:
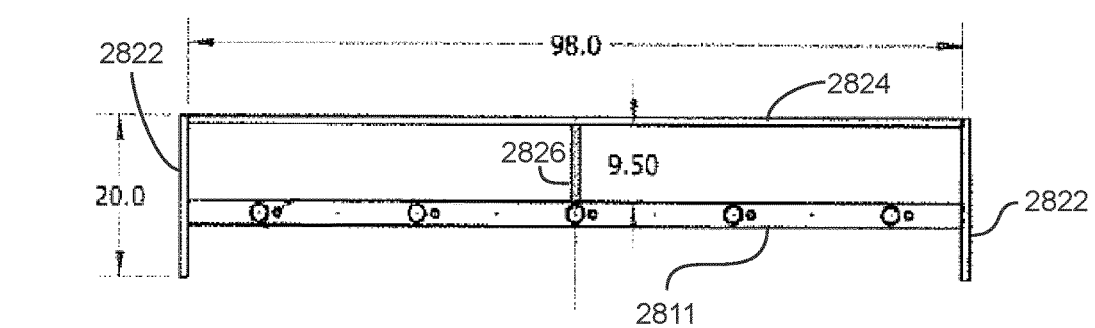
FIG. 20 is a top view of a base frame of the seating assembly of FIG. 1, according to an exemplary embodiment.
Figure 21:
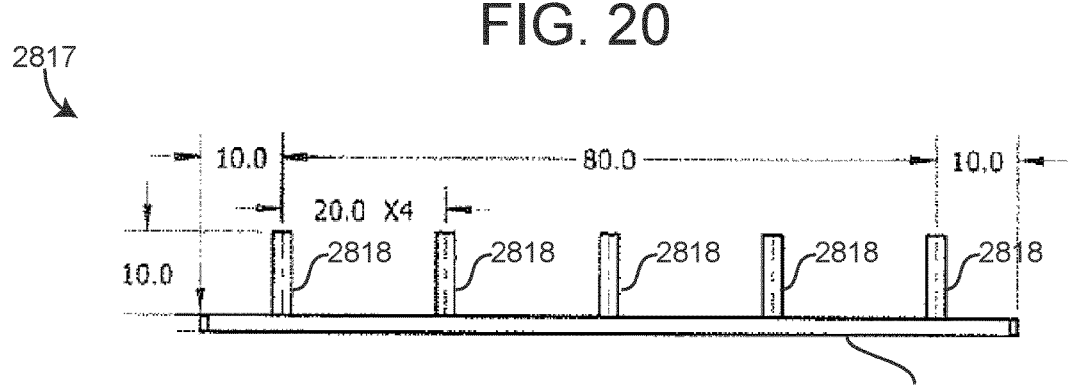
FIG. 21 is a front view of a base frame of the seating assembly of FIG. 1, according to an exemplary embodiment.

Referring now to FIGS. 19-21, support frame 2817 is shown in greater detail, according to an exemplary embodiment. Support frame 2817 includes five seat support members 2818, configured to support seats 102a-102e. Support frame 2817 includes central support member 2811, side support members 2822, cross support member 2826, and outer support member 2824. In an exemplary embodiment, central support member 2811, side support members 2822, cross support member 2826, and outer support member 2824 have dimensions and configuration as shown in FIGS. 20-21 where the dimensions are in units of inches. In an exemplary embodiment, support frame 2817 is contained within a housing. In some embodiments, the housing and support frame 2817 define base 108.

Heating Elements

Referring now to FIGS. 24-25 and 27-28, the configuration and function of heating pads 156/164 is shown in greater detail, according to an exemplary embodiment. Heating pads 156/164 are positioned either adjacent an exterior surface of seat cushion 198/back cushion 196 or within seat cushion 198/back cushion 196, respectively. Heating pads 156 are configured to provide heat to a torso of a user, and heating pads 164 are configured to provide heat to lower limbs of the user. Heating pads 156 are provided with electrical energy through cords 2302, according to an exemplary embodiment. Cords 2302 may run through an inner volume of any tubular members of seat frame 2807. In an exemplary embodiment, controller 2400 provides heating pads 156 with power via cords 2302 and/or heating pads 164 with power via cords 2402. Cords 2402 electrically and communicably connect controller 2400 with heating pads 164. In an exemplary embodiment, cords 2402 run through an inner volume of tubular members of seat frame 2807 to controller 2400. In an exemplary embodiment, controller 2400 receives power through cords which run through support frame 2817.

Figure 25:
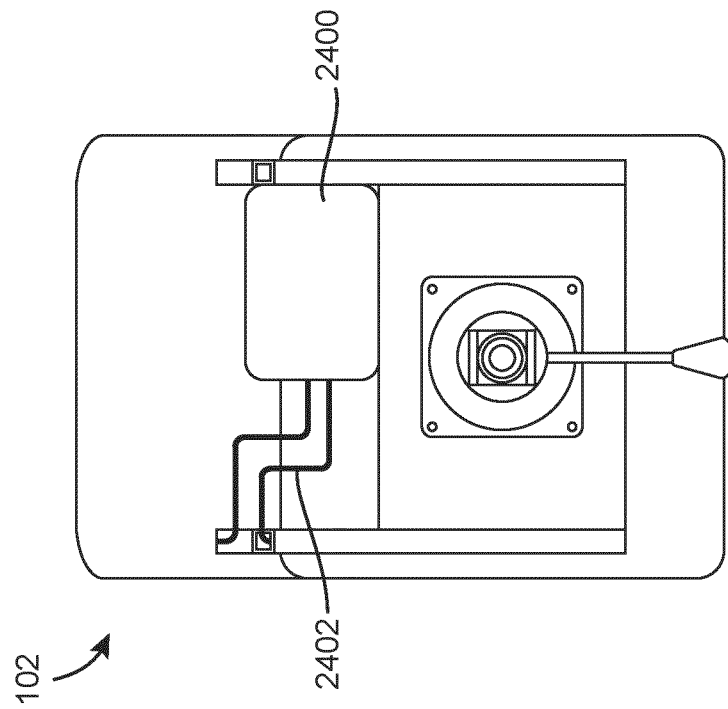
FIG. 25 is a bottom view diagram of a seat of the seating assembly of FIG. 1, according to an exemplary embodiment.
Figure 24:
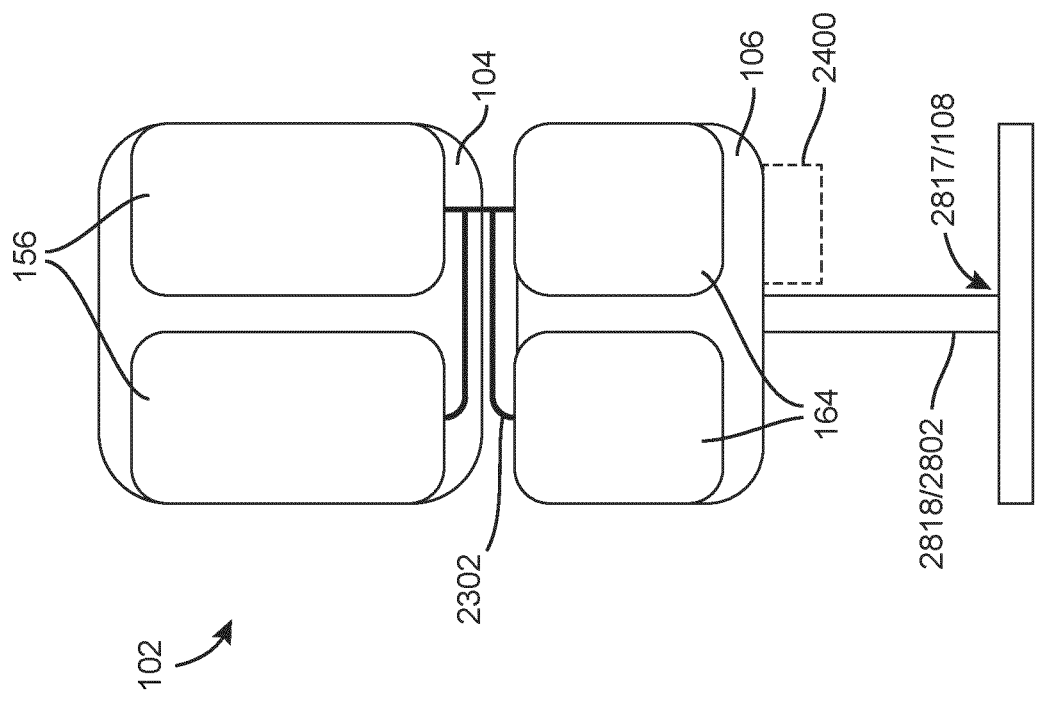
FIG. 24 is a front view diagram of heating elements of a seating of the seat assembly of FIG. 1, according to an exemplary embodiment.

FIG. 25 shows a bottom view of one of seats 102, according to an exemplary embodiment. Controller 2400 may be contained within a housing mounted to a bottom surface of seat 102. Controller 2400 is configured to adjust an operation of the corresponding adjustable support member 110 for seat 102 as well as an amount of heat/a rate of heat produced by heating pads 164 and heating pads 156.

Figure 27:
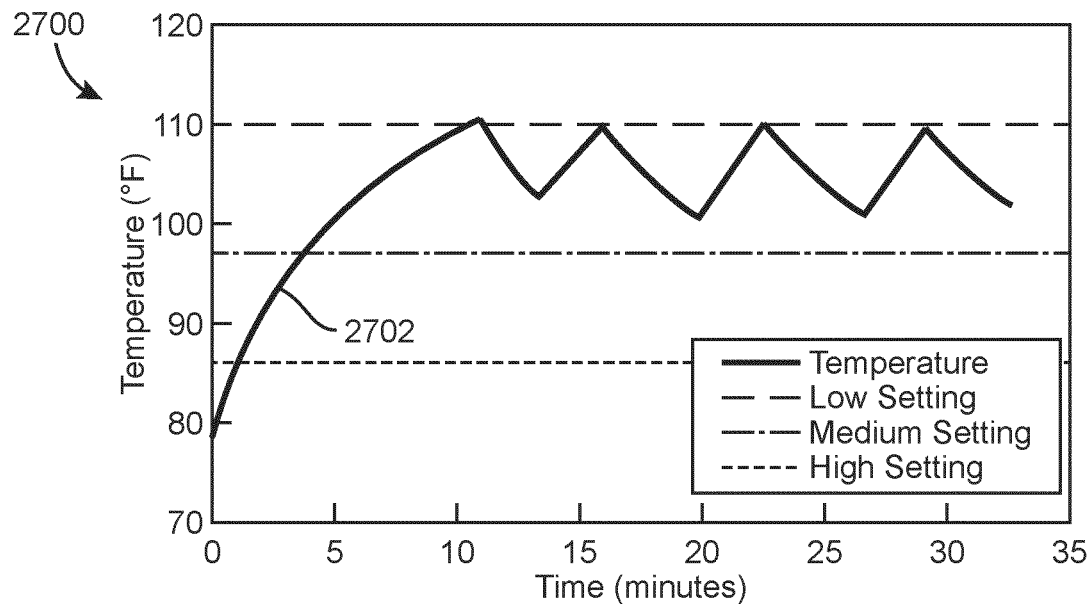
FIG. 27 is a graph illustrating the operation of the heating elements of the seating assembly of FIG. 1, according to an exemplary embodiment.

FIG. 27 shows a graph 2700 which illustrates heat output (i.e., surface temperature) of either heating pads 156 or heating pads 164, according to an exemplary embodiment. Controller 2400 is configured to transition heating pads 164 between an on state and an off state. Series 2702 illustrates the change in temperature of heating pads 156 and/or heating pads 164. The Y-axis of graph 2700 represents temperature, and the X-axis represents time in minutes. Series 2702 represents operation of heating pads 156 and/or heating pads 164 in a high heating mode of operation. As shown in graph 2700, series 2702 increases to a maximum temperature for approximately 10 minutes. Controller 2400 actuates heating pads 156 and/or heating pads 164 between the on state and the off state to maintain temperature at approximately the maximum temperature, as shown in graph 2700. Controller 2400 operates similarly for any of the medium heating mode and the low heating mode.

Figure 28:
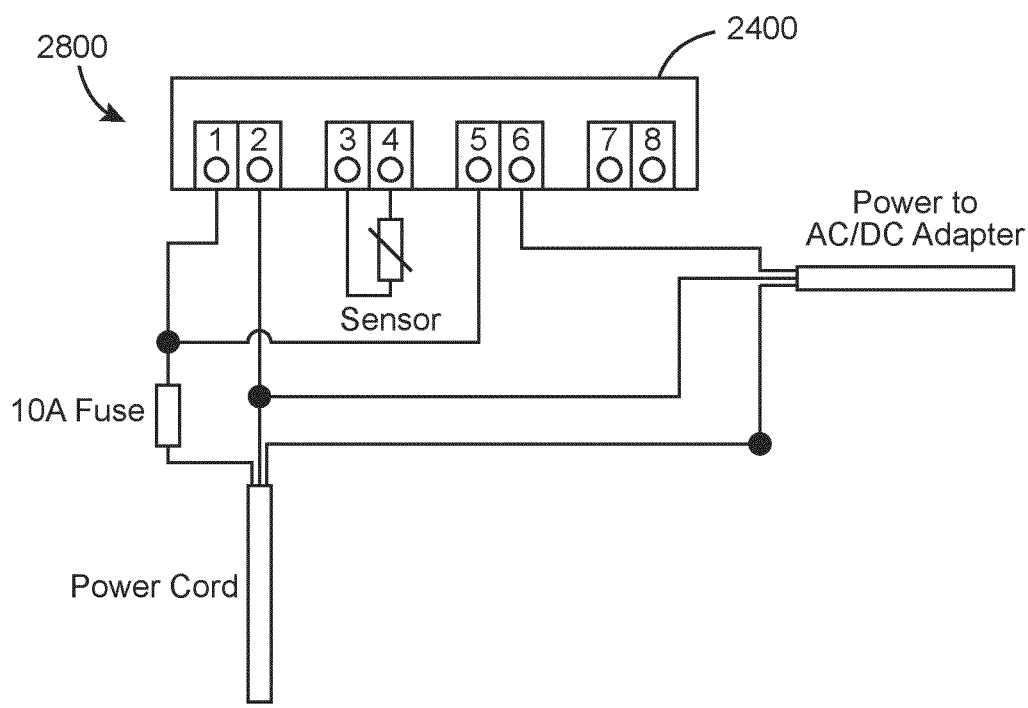
FIG. 28 is a schematic illustrating an electrical system of the heating elements of the seating assembly of FIG. 1, according to an exemplary embodiment.

FIG. 28 shows an electrical diagram 2800 for controller 2400, according to an exemplary embodiment. Controller 2400 receives temperature feedback from a temperature sensor. The temperature sensor is configured to measure temperature of either one of or both heating pads 156 and heating pads 164 and provide controller 2400 with the measured temperature values, according to an exemplary embodiment. Controller 2400 receives power from a power cord which receives power from a power source (e.g., a wall outlet, a generator). The power received by controller 2400 may be 120 volt AC power. Controller 2400 may include a 10 amp fuse to ensure that controller 2400 does not experience surges in power from the power source. Controller 2400 uses any of the power supplied by the power source to adjust an operation of adjustable support members 110 to increase or decrease in length and to adjust an operation of at least one of heating pads 156 and heating pads 164 to increase or decrease a temperature and/or a heat produced by heating pads 156 and/or heating pads 164. In some embodiments, cords which are used to connect controller 2400 to any devices, systems, sensors, etc., of seating assembly 100 pass through inner volumes of one or more tubular members of seating assembly 100.

Referring to FIGS. 28-29, controller 2400 may monitor the status (e.g., the temperature) of heating pads 156/164. Controller 2400 may include a power interface 3008 configured to receive power from a power source and provide power (e.g., DC power) to heating pads 156/164 and/or adjustable support members 110. Controller 2400 may also include a transformer configured to step up or step down voltage of power provided to heating pads 156/164 and/or adjustable support members 110. Controller 2400 may also include a processing circuit 3002 configured to perform any of the functions of controller 2400 described herein. Controller 2400 also includes a communications interface 3010 (e.g., a USB interface, a serial communications interface, etc.) configured to receive information from any temperature sensors, height sensors, user input devices, etc. Controller 2400 may use the received temperature information and/or commands from the input devices to determine whether to adjust an operation of heating pads 156 and/or heating pads 164, according to an exemplary embodiment. For example, controller 2400 may receive a command from the user interface to increase heat or a temperature of heating pads 156 and/or heating pads 164. Controller 2400 may use the command received from the user interface device to adjust an operation of heating pads 156 and/or heating pads 164 to increase the temperature. In an exemplary embodiment, controller 2400 may receive a command to transition heating pas 156 and/or heating pads 164 between various predefined modes of operation (e.g., high heating mode, medium heating mode, low heating mode, etc.).

Processing circuit 3002 may include a processor 3004 and memory 3006. Processor 3004 may be a general purpose or specific purpose processor, an application specific integrated circuit (ASIC), one or more field programmable gate arrays (FPGAs), a group of processing components, or other suitable processing components. Processor 3004 may be configured to execute computer code or instructions stored in memory or received from other computer readable media (e.g., CDROM, network storage, a remote server, etc.).

Memory 3006 may include one or more devices (e.g., memory units, memory devices, storage devices, etc.) for storing data and/or computer code for completing and/or facilitating the various processes described in the present disclosure. Memory 3006 may include random access memory (RAM), read-only memory (ROM), hard drive storage, temporary storage, non-volatile memory, flash memory, optical memory, or any other suitable memory for storing software objects and/or computer instructions. Memory 3006 may include database components, object code components, script components, or any other type of information structure for supporting the various activities and information structures described in the present disclosure. Memory 3006 may be communicably connected to processor 3004 via processing circuit 3002 and may include computer code for executing (e.g., by processor 3004) one or more processes described herein.

In some embodiments, any of the electrical components, elements, members, etc., (e.g., controller 2400, heating pads 154, heating pads 156, prime mover 2819, screens 162, etc.) are configured to draw power from a power system or a cord that extends through base 108 (e.g., through support frame 2817). The cord may be plugged into a wall outlet or other power source to provide electrical energy to the various electrical components or electrical consuming elements of seating assembly 100. If multiple seating assemblies 100 are arranged next to each other, the seating assemblies 100 may each be plugged into a wall outlet, or other power source, or may be plugged into each other (e.g., serially), with one of the seating assemblies 100 being plugged into a single wall outlet or other power source.

Control Panel

Figure 26:
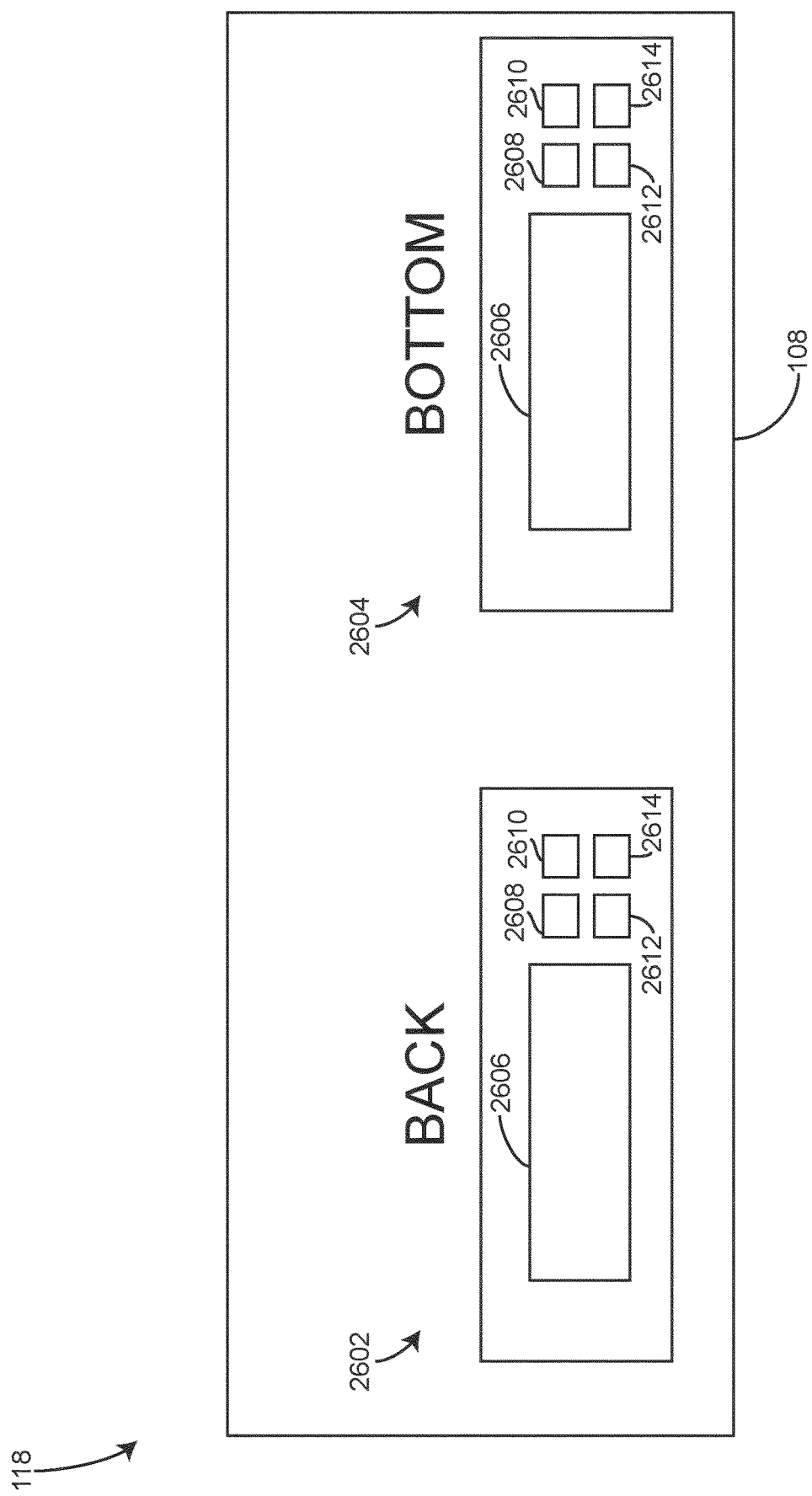
FIG. 26 is a perspective view of a control panel of a seat of the seating assembly of FIG. 1, according to an exemplary embodiment.

Referring now to FIG. 26, one of adjustment interfaces 118 is shown in greater detail, according to an exemplary embodiment. Adjustment interface 118 includes a first user interface 2602 and a second user interface 2604. In some embodiments, adjustment interface 118 is a component of controller 2400. Adjustment interface 118 may be positioned at base 108, or at a bottom of seat 102. Controller 2400 receives user inputs via adjustment interface 118. For example, controller 2400 may receive commands from user interfaces 2602 and 2604 to start controller 2400 (e.g., by pressing power on button 2608), increase the temperature (e.g., by pressing increase button 2610), decrease the temperature (e.g., by pressing decrease button 2614), or to select an operation of controller 2400 (e.g., by pressing selection button 2612). In an exemplary embodiment, heat provided to the torso (e.g., via heating pads 156) and to the lower limbs (e.g., via heating pads 164) can be individually adjusted via user interface 2602 and user interface 2604, respectively. For example, user interface 2602 may be configured to adjust an operation of heating pads 156, and user interface 2604 may be configured to adjust an operation of heating pads 164 (i.e., increase or decrease temperature by some amount). In other embodiments, only one user interface is used, and the single user interface is configured to adjust the operation of both heating pads 164 and heating pads 156 simultaneously.

User interfaces 2602 and 2604 also include a display screen 2606, according to an exemplary embodiment. Display screen is configured to display a current temperature or heat produced by either one of or both heating pads 156 and heating pads 164. For example, display screen 2606 may display a current temperature produced by heating pads 156 and/or heating pads 164.

The current temperature may be measured by a single or multiple temperature sensors. The temperature sensor(s) may be installed within seat portion 106 and/or back portion 104. In an exemplary embodiment, display screen 2606 displays a current temperature as measured by the single or multiple temperatures. In some embodiments, display screen 2606 displays a temperature setpoint which controller 2400 is set to achieve. The temperatures as measured by the temperature sensor(s) can be used by controller 2400 as feedback to determine when to transition heating pads 156 and/or heating pads 164 between the on state and the off state to maintain a current temperature setpoint. For example, if the temperature setpoint is 110 degrees Fahrenheit, controller 2400 provides heating pads 164 and/or heating pads 156 with power until the temperature measured by corresponding temperature sensors is the setpoint. Controller 2400 then cuts off power to heating pads 156 and/or heating pads 164. Once the measured temperature decreases a predetermined threshold amount below the temperature setpoint (e.g., 1 degree Fahrenheit below 110 degrees Fahrenheit), controller 2400 resumes providing heating pads 156 and/or heating pads 164 with power. This process can be repeated to maintain an average setpoint temperature over a time period.

Adjustable Support Members

Referring again to FIG. 29, adjustable support member 110 is shown in greater detail, according to an exemplary embodiment. Adjustable support member 110 may be configured to adjust in height. In some embodiments, adjustable support member 110 includes movable member 2802 and seat support member 2818. Movable member 2802 is configured to move (e.g., translate relative to seat support member 2818 to increase or decrease an overall height of adjustable support member 110. In some embodiments, movable member 2802 is configured to move relative to seat support member 2818 in response to a manual input from a user via adjustment lever 2902. In some embodiments, adjustable support member 110 is a manual system, which does not require controller 2400 to operate. For example, adjustable support member 110 may be a gas-charged spring, configured to facilitate movement of movable member 2802 relative to seat support member 2818 in response to an actuation of adjustment lever 2902. In other embodiments, adjustable support member 110 is configured to adjust in overall length due to an operation of a prime mover (e.g., an electric motor, a hydraulic system, etc.), shown as prime mover 2819. In some embodiments, prime mover 2819 is configured to move (e.g., translate) movable member 2802 relative to seat support member 2818. In some embodiments, prime mover 2819 adjusts an overall length of adjustable support member 110 in response to a user input. The user input may be received by controller 2400 via adjustment interface 118. Controller 2400 may receive the user input (e.g., a command to increase overall height of adjustable support member 110 or to decrease overall height of adjustable support member 110) and cause prime mover 2819 to adjust the overall height of adjustable support member 110 by translating movable member 2802 relative to seat support member 2818.

In some embodiments, movable member 2802 is or includes a piston, configured to slidingly interface within a surface of an inner volume of seat support member 2818. In other embodiments, movable member 2802 is configured to interface with seat support member 2818 via any of a groove, track, notch, etc., which runs along a length of movable member 2802 and/or seat support member 2818. For example, movable member 2802 or seat support member 2818 may include one or more protrusions which run along a length of movable member 2802 or seat support member 2818 and are configured to interface with a corresponding track or groove of movable member 2802 or seat support member 2818.

In some embodiments, movable member 2802 can translate relative to seat support member 2818 a distance of 10 inches or greater. In some embodiments, movable member 2802 being configured to translate relative to seat support member 2818 facilitates changing (e.g. increasing or decreasing) distance 2820 at least 10 inches. In some embodiments, distance 2820 between an upper surface of seat portion 106 and a floor surface upon which base 108 rests is at least 18 inches. Advantageously, seat 102 being configured to increase in height (e.g., distance 2820) 10 inches or greater facilitates an optimal popliteal distance (e.g., popliteal height 716) for a tall user (e.g., a basketball player). This reduces the likelihood of restricted venous blood flow which may occur if the popliteal distance is too small, particularly for tall athletes such as basketball players.

Performance Testing

Seating assembly 100 advantageously increases venous blood flow to the trunk/torso and lower limbs of one or more users, according to an exemplary embodiment. Seating assembly 100 includes adjustable height and adjustable heating to both facilitate adjusting angles 708 and 715, as well as to provide some amount of heat to the user. Both adjusting angles 708 and 715 as well as providing some amount of heat to the one or more users facilitates venous blood flow of the one or more users. Advantageously, if seating assembly 100 is used in a sporting application or for any other users who will be exercising/exerting themselves, the increased venous blood flow facilitates better performance of the users in the sporting event. Seating assembly 100 may facilitate players maintaining metabolic homeostasis better than other bench chairs/seating assemblies which do not include adjustable heating and adjustable height. Referring to FIGS. 8-12, graphs 800-1200 demonstrate advantages of the adjustable height/heating seating assembly 100 versus other seats which do not have adjustable heat and adjustable height, according to an exemplary embodiment. Graphs 800-1200 illustrate test results of sixteen basketball players, demonstrating that seating assembly 100 improves shuttle run time, vertical jump distance, skin temperature, and heart rate as compared to a control seating assembly which does not include adjustable height and adjustable heating. First, the sixteen basketball players warmed up (stretching, jogging, etc.).

Next, the players performed a shuttle run, and the amount of time for each player to complete the shuttle run was recorded ($t_{i,control}$). After a 10 second break, the players each performed three vertical jumps with five seconds of rest in between each jump. The height of each jump was recorded using a Vertec vertical jump apparatus and an average jump height ($h_{i,control}$) was determined. After the vertical jumps were completed, skin temperature of each of the players was measured ($T_{i,control}$). The skin temperature was measured at the hamstring of each player. Then, the heart rate ($r_{i,control}$) of each player was recorded over ten seconds (taken at the neck). The players then rested in the control seating assembly for 10 minutes. The testing was then performed again after the players had rested in the control seating assembly for 10 minutes to determine final values of the amount of time for each player to complete the shuttle run $t_{f,control}$, average jump height $h_{f,control}$, skin temperature $T_{f,control}$, and heart rate $r_{f,control}$. Using the information from before and after resting in the control seating assembly, a percent increase (or decrease) is determined for the control seating assembly.

Similar tests were performed for seating assembly 100. The players adjusted seats 102 of seating assembly 100 to a comfortable height such that angle 714 of each player was equal to or greater than 90 degrees. The same testing was performed for seating assembly 100 as the control seating assembly to determine $t_{i,test}$, $t_{f,test}$, $h_{i,test}$, $h_{f,test}$, $T_{i,test}$, $T_{f,test}$, $r_{i,test}$, and $r_{f,test}$. Using the test results from before the ten-minute rest period and after the ten-minute rest period, percent increase (or decrease) for seating assembly 100 can be determined.

Graphs 800-1100 show the percent improvement for each of the 16 players. In graph 800, series 802 represents percent improvement of the shuttle run time for the control seating assembly and series 804 represents percent improvement of the shuttle run time for seating assembly 100. Likewise, in graph 900, series 902 represents percent improvement of the vertical jump height for the control seating assembly and series 904 represents percent improvement of the vertical jump height for seating assembly 100. In graph 1000, series 1002 represents percent improvement of skin temperature for the control seating assembly and series 1004 represents percent improvement of skin temperature for seating assembly 100. In graph 1100, series 1102 represents improvement of heart rate for the control seating assembly and series 1104 represents percent improvement of heart rate for seating assembly 100.

Figure 12:
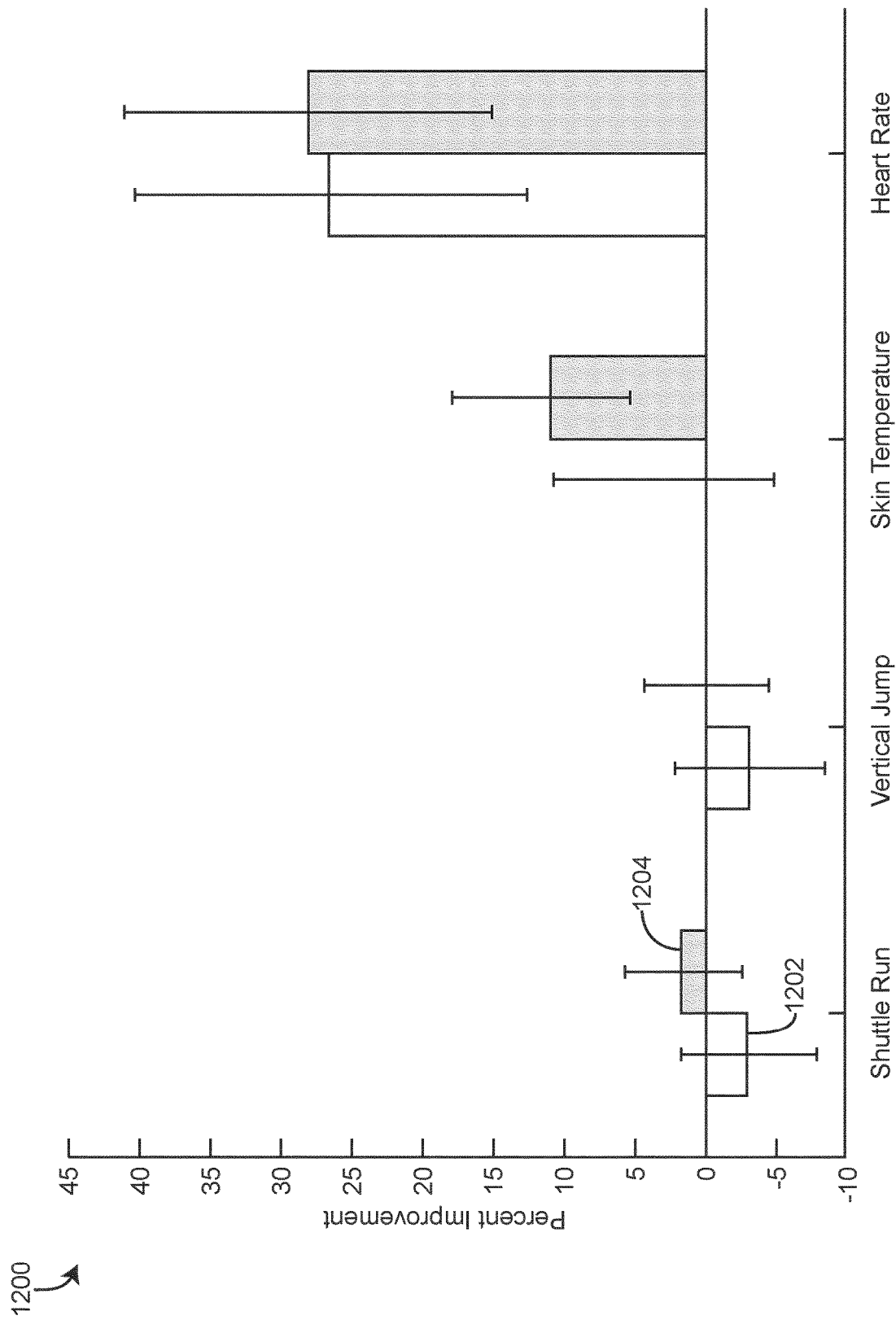
FIG. 12 is graph of average test results of the graphs of FIGS. 8-11, according to an exemplary embodiment.

Graphs 800-1100 demonstrate a large amount of variation. In order to quantify if seating assembly 100 improves any of the shuttle run time, the average vertical jump height, skin temperature, and heart rate, an ANOVA test can be performed. FIG. 12 includes graph 1200 which shows average percent improvement and standard deviations for both the control seating assembly and seating assembly 100, according to some embodiments. Series 1202 of graph 1200 illustrates average percent improvement for the control seating assembly for each of shuttle run time, average vertical jump height, skin temperature, and heart rate. Series 1204 of graph 1200 illustrates average percent improvement for seating assembly 100 for each of shuttle run time, average vertical jump height, skin temperature, and heart rate. Graph 1200 shows series 1204 having a larger percent improvement than series 1202 for each of the shuttle run time, the average vertical jump height, skin temperature, and heart rate. For example, for the shuttle run time, the control seating assembly (series 1202) resulted in a negative percent improvement, while seating assembly 100 resulted in a positive percent improvement.

The results of both a MANOVA test, as well as individual ANOVA test for each performance measure (shuttle run time, average vertical jump height, skin temperature, and heart rate) is shown in Table 1 below:

TABLE 1

| Hypothesis Test | α | Confidence Interval | p-value | Conclusion |
| --- | --- | --- | --- | --- |
| One-way MANOVA | 0.1 | 90% | 0.011 | Statistically significant |
| One-way ANOVA - Shuttle Run | 0.1 | 90% | 0.008 | Statistically significant |
| One-way ANOVA - Vertical Jump | 0.1 | 90% | 0.086 | Statistically significant |
| One-way ANOVA - Skin Temperature | 0.1 | 90% | 0.019 | Statistically significant |
| One-way ANOVA - Heart Rate | 0.1 | 90% | 0.019 | Statistically significant |

As shown in Table 1 above, there is a statistically significant difference between the percent improvement for each of the shuttle run time, the average vertical jump height, skin temperature, and heart rate for seating assembly 100. The percent improvement shows that seating assembly 100 improves metabolic homeostasis by both providing heat to the players, as well as facilitating more venous blood flow due to improved angle 714 and angle 708. Additionally, some seating assemblies such as the control seating assembly do not facilitate improved angle 714 and angle 708. This may result in restricted blood flow and a decreased amount of venous blood flow to lower limbs particularly. As shown in FIGS. 8-12, seating assembly 100 advantageously improves metabolic homeostasis and can improve athletic performance.

Configuration of Exemplary Embodiments

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, and/or illustrations of possible embodiments (and such terms are not intended to connote that such embodiments are necessarily extraordinary or superlative examples).

The term "coupled," as used herein, means the joining of two members directly or indirectly to one another. Such joining may be stationary (e.g., permanent or fixed) or movable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. Such members may be coupled mechanically, electrically, and/or fluidly.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

The hardware and data processing components used to implement the various processes, operations, illustrative logics, logical blocks, modules and circuits described in connection with the embodiments disclosed herein may be implemented or performed with a general purpose single- or multi-chip processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, such as a combination of a DSP and a microprocessor, a plurality of microprocessors, one or more microprocessors in conjunction with a DSP core, or any other such configuration. In some embodiments, particular processes and methods may be performed by circuitry that is specific to a given function. The memory (e.g., memory, memory unit, storage device, etc.) may include one or more devices (e.g., RAM, ROM, Flash memory, hard disk storage, etc.) for storing data and/or computer code for completing or facilitating the various processes, layers and modules described in the present disclosure. The memory may be or include volatile memory or non-volatile memory, and may include database components, object code components, script components, or any other type of information structure for supporting the various activities and information structures described in the present disclosure. According to an exemplary embodiment, the memory is communicably connected to the processor via a processing circuit and includes computer code for executing (e.g., by the processing circuit and/or the processor) the one or more processes described herein.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

It is important to note that the construction and arrangement of the fire suppression system as shown in the various exemplary embodiments is illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. Other substitutions, modifications, changes, and omissions may be made in the design, operating conditions and arrangement of the exemplary embodiments without departing from the scope of the present disclosure.

Additionally, any element disclosed in one embodiment may be incorporated or utilized with any other embodiment disclosed herein. For example, the adjustment interface 118 as described with reference to FIG. 26 may be implemented in the embodiment of seat 102 as described with reference to FIG. 24. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A seating assembly for one or more athletes, the seating assembly comprising:
   a movable base;
   a plurality of seats coupled to the movable base, each seat of the plurality of seats comprising:
      a back portion;
      a seat portion coupled to the back portion;
      a heating member configured to provide heat to a user;
      an adjustable element coupling the movable base to the seat portion and configured to adjust a height of the seat relative to the movable base;
      a controller configured to:
         control operation of the heating member to achieve a desired temperature based on a first input; and
         control operation of the adjustable element to adjust the height of the seat relative to the movable base based on a second input.

2. The seating assembly of claim 1, wherein the heating member comprises a back heating member provided in the back portion and configured to provide heat to a torso of the user, and a lower limb heating member provided in the seat portion and configured to provide heat to lower limbs of the user.

3. The seating assembly of claim 2, wherein the back heating member is positioned within a cushion of the back portion and the lower limb heating member is positioned within a cushion of the seat portion.

4. The seating assembly of claim 1, wherein each seat of the plurality of seats further comprises a sensor configured to measure a temperature of the heating member, and wherein the controller is configured to control operation of the heating member based on the temperature.

5. The seating assembly of claim 1, wherein the adjustable element comprises a telescoping pedestal.

6. The seating assembly of claim 1, wherein the adjustable element comprises an electric motor or a hydraulic system.

7. The seating assembly of claim 1, wherein each of the plurality of seats is configured to increase in height relative to a floor surface at least ten inches to facilitate a popliteal height of at least 18 inches of the user.

8. The seating assembly of claim 1, further comprising a user interface configured to receive the first input and the second input from the user.

9. A seating assembly for one or more users, the seating assembly comprising:
   a movable base;
   a plurality of seats coupled to the movable base, each of the plurality of seats comprising:
      a back portion comprising a back cushion and a back heating element positioned within the back cushion, wherein the back heating element and the back cushion are configured to transfer heat to a torso of a user;
      a seat portion comprising a seat cushion and a seat heating element positioned within the seat cushion, wherein the seat heating element and the seat cushion are configured to transfer heat to lower limbs of the user; and
      a controller configured to receive an input regarding a desired temperature of at least one of the back heating element and the seat heating element and further configured to control operation of the at least one of the back heating element and the seat heating element based on the input;
      wherein the movable base further comprises a plurality of openings configured to receive one or more elongated members of a transportation mechanism for movement of the seating assembly.

10. The seating assembly of claim 9, further comprising a support member coupled to the seat portion and the movable base and configured to enable adjustment of the seat relative to the movable base.

11. The seating assembly of claim 10, wherein the input is a first input, and wherein the controller is configured to receive a second input regarding a desired height of the seat and control operation of the support member based on the second input.

12. The seating assembly of claim 11, wherein the support member comprises a telescoping pedestal.

13. The seating assembly of claim 9, wherein the back heating element is configured to heat the torso of the user to a temperature between 38 and 45 degrees Celsius to facilitate venous blood flow to the torso of the user and the seat heating element is configured to heat the lower limbs of the user to a temperature between 38 and 45 degrees Celsius to facilitate venous blood flow to the lower limbs of the user.

14. The seating assembly of claim 9, further comprising a user interface configured to receive the input from the user.

15. A method for installing and operating a seating assembly, the method comprising:
   providing a seating assembly comprising a plurality of seats coupled to a movable base, wherein each of the plurality of seats is configured to provide at least one of adjustable heating and an adjustable height for a user;
   positioning the seating assembly in a desired location;
   connecting the seating assembly to a power source for the at least one of adjustable heating and the adjustable height of each of the plurality of seats;
   receiving an input from a user interface of one of the plurality of seats;
   based on the input, adjusting at least one of:
      an amount of heat provided to the user via a heating pad disposed within the one of the plurality of seats; and
      a height of the one of the plurality of seats, wherein adjusting the height comprises changing a distance between a seat portion and a floor surface to between a minimum value of the distance and a maximum value of the distance;

wherein a back portion and the seat portion of each of the plurality of seats form an angle greater than ninety degrees.

16. The method of claim 15, wherein the angle formed by the back portion and the seat portion is between 110 and 120 degrees to improve venous blood flow to lower limbs of the user.

17. The method of claim 15, wherein the heat provided to the user is provided to heat at least one of a torso and lower limbs of the user to a temperature between 38 and 45 degrees Celsius to facilitate venous blood flow.

18. The method of claim 15, further comprising:

inserting one or more fork members into one or more apertures of the movable base; and lifting the seating assembly via the one or more fork members inserted into the one or more apertures for removal and placement of the seating assembly.

* * * * *